(12) United States Patent
Burkett

(10) Patent No.: US 10,932,678 B2
(45) Date of Patent: *Mar. 2, 2021

(54) MOUNTING STRUCTURES FOR COMPONENTS OF INTRAVASCULAR DEVICES

(71) Applicant: PHILIPS IMAGE GUIDED THERAPY CORPORATION, San Diego, CA (US)

(72) Inventor: David Burkett, Panama Beach, FL (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 236 days.

This patent is subject to a terminal disclaimer.

(21) Appl. No.: 15/986,690

(22) Filed: May 22, 2018

(65) Prior Publication Data

US 2018/0263509 A1    Sep. 20, 2018

Related U.S. Application Data

(63) Continuation of application No. 14/014,868, filed on Aug. 30, 2013, now Pat. No. 9,974,446.

(Continued)

(51) Int. Cl.
*A61B 5/00* (2006.01)
*A61B 5/0215* (2006.01)
(Continued)

(52) U.S. Cl.
CPC .......... *A61B 5/0215* (2013.01); *A61B 5/6851* (2013.01); *A61B 18/1492* (2013.01);
(Continued)

(58) Field of Classification Search
CPC ..... A61B 5/0215; A61B 18/1492; A61B 8/12; A61B 5/02007; A61B 5/6851; A61B 5/6852; A61M 25/09; A61M 2025/0002
(Continued)

(56) References Cited

U.S. PATENT DOCUMENTS 4,873,986 A * 10/1989 Wallace ................. A61B 5/035
                                                    600/483
4,953,553 A *  9/1990 Tremulis ............. A61B 5/0215
                                                    600/434

(Continued)

FOREIGN PATENT DOCUMENTS

EP      1479407 A1   11/2004
JP     11076179 A    3/1999
(Continued)

OTHER PUBLICATIONS

International Search Report and Written Opinion Received in Patent Cooperation Treaty Application No. PCT/US2013/057696, dated Dec. 23, 2013, 14 pages.
(Continued)

*Primary Examiner* — May A Abouelela

(57) ABSTRACT

Intravascular devices, systems, and methods are disclosed. In some embodiments, the intravascular devices include at least one mounting structure within a distal portion of the device. In that regard, one or more electronic, optical, and/or electro-optical component is coupled to the mounting structure. In some instances, the mounting structure is formed of a plurality of material layers. In some embodiments, the material layers have substantially constant thicknesses. Methods of making and/or assembling such intravascular devices/systems are also provided.

21 Claims, 10 Drawing Sheets

Related U.S. Application Data

(60) Provisional application No. 61/695,970, filed on Aug. 31, 2012.

(51) Int. Cl.
| | | |
|---|---|---|
| A61M 25/09 | (2006.01) | |
| A61M 25/00 | (2006.01) | |
| A61B 18/14 | (2006.01) | |
| A61B 17/22 | (2006.01) | |
| A61B 90/00 | (2016.01) | |

(52) U.S. Cl.
CPC ............ *A61B 2017/22042* (2013.01); *A61B 2090/064* (2016.02); *A61B 2562/0247* (2013.01); *A61M 25/09* (2013.01); *A61M 2025/0002* (2013.01); *A61M 2025/09183* (2013.01)

(58) Field of Classification Search
USPC ............... 600/585, 486, 488, 561; 604/523
See application file for complete search history.

(56) References Cited

U.S. PATENT DOCUMENTS

| | | | | |
|---|---|---|---|---|
| 4,964,409 A * | 10/1990 | Tremulis | ............. | A61B 5/0215 600/434 |
| 5,018,529 A * | 5/1991 | Tenerz | ............... | A61B 5/02154 600/480 |
| 5,050,606 A * | 9/1991 | Tremulis | ............... | A61B 5/021 600/486 |
| 5,085,223 A * | 2/1992 | Lars | ..................... | G01L 9/0077 600/488 |
| 5,226,423 A * | 7/1993 | Tenerz | ................. | A61B 5/0215 600/486 |
| 5,715,827 A * | 2/1998 | Corl | .................... | A61B 5/0215 600/486 |
| 6,112,598 A | 9/2000 | Tenerz | | |
| 6,142,958 A * | 11/2000 | Hammarstrom | ..... | A61B 5/6851 600/486 |
| 6,663,570 B2 * | 12/2003 | Mott | ................... | A61B 5/0215 439/909 |
| 7,263,894 B2 * | 9/2007 | Tenerz | ................. | A61B 5/0215 600/585 |
| 7,472,601 B1 * | 1/2009 | Tenerz | ................. | A61B 5/0215 600/585 |
| 7,967,761 B2 * | 6/2011 | Smith | .................... | A61B 5/036 600/585 |
| 8,231,537 B2 * | 7/2012 | Ahmed | ............. | A61B 5/02158 600/485 |
| 8,579,825 B2 * | 11/2013 | Tenerz | .................. | A61M 25/09 600/488 |
| 9,095,685 B2 * | 8/2015 | Sela | .......................... | A61B 5/06 |
| 2003/0141783 A1 | 7/2003 | Klee | | |
| 2003/0143268 A1 | 7/2003 | Pryce Lewis | | |
| 2003/0220588 A1 * | 11/2003 | Tenerz | ................. | A61B 5/6851 600/585 |
| 2005/0268725 A1 | 12/2005 | Tulkki | | |
| 2006/0074318 A1 * | 4/2006 | Ahmed | .................. | A61B 8/445 600/465 |
| 2006/0241505 A1 | 10/2006 | Ahmed | | |
| 2006/0264904 A1 | 11/2006 | Kerby | | |
| 2007/0003427 A1 | 1/2007 | Yamamoto | | |
| 2007/0106165 A1 * | 5/2007 | Tulkki | ................. | A61B 5/0215 600/486 |
| 2007/0255217 A1 * | 11/2007 | Burkett | ................... | B29C 48/05 604/164.13 |
| 2008/0077050 A1 * | 3/2008 | Von Malmborg | ... | A61B 5/6851 600/585 |
| 2009/0062602 A1 * | 3/2009 | Rosenberg | ........ | A61M 25/0141 600/101 |
| 2009/0088650 A1 | 4/2009 | Corl | | |
| 2010/0204560 A1 * | 8/2010 | Salahieh | .............. | A61B 5/0422 600/373 |
| 2011/0015533 A1 * | 1/2011 | Cox | ..................... | A61B 8/0841 600/509 |
| 2011/0244010 A1 | 10/2011 | Doshi | | |
| 2011/0251497 A1 | 10/2011 | Corl | | |
| 2012/0191121 A1 | 7/2012 | Chen | | |
| 2013/0053730 A1 * | 2/2013 | Kotlanka | .......... | A61M 25/0082 600/585 |

FOREIGN PATENT DOCUMENTS

| | | |
|---|---|---|
| JP | 11076183 A | 3/1999 |
| JP | 2001239592 A | 9/2001 |
| WO | 2011123180 A1 | 10/2011 |
| WO | 2012000798 A1 | 1/2012 |

OTHER PUBLICATIONS

International Searching Authrity/Eurpean Patent Office, "Supplementary European Search Report," for EP Application No. 13833102.0, dated Mar. 18, 2016, 7 pages.

\* cited by examiner

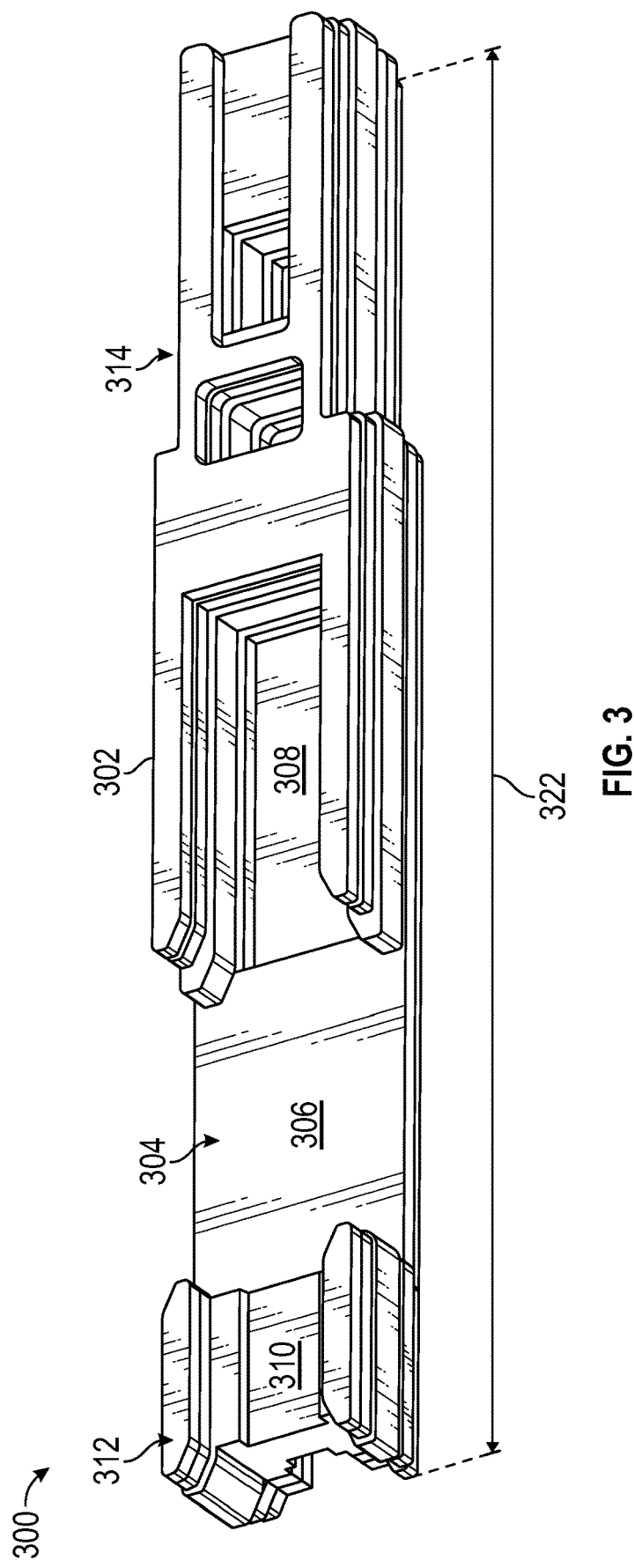

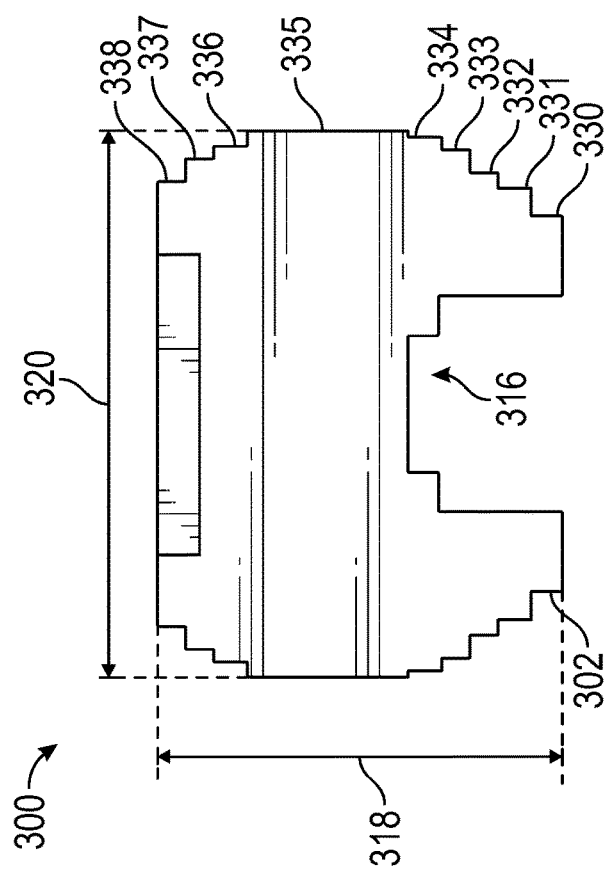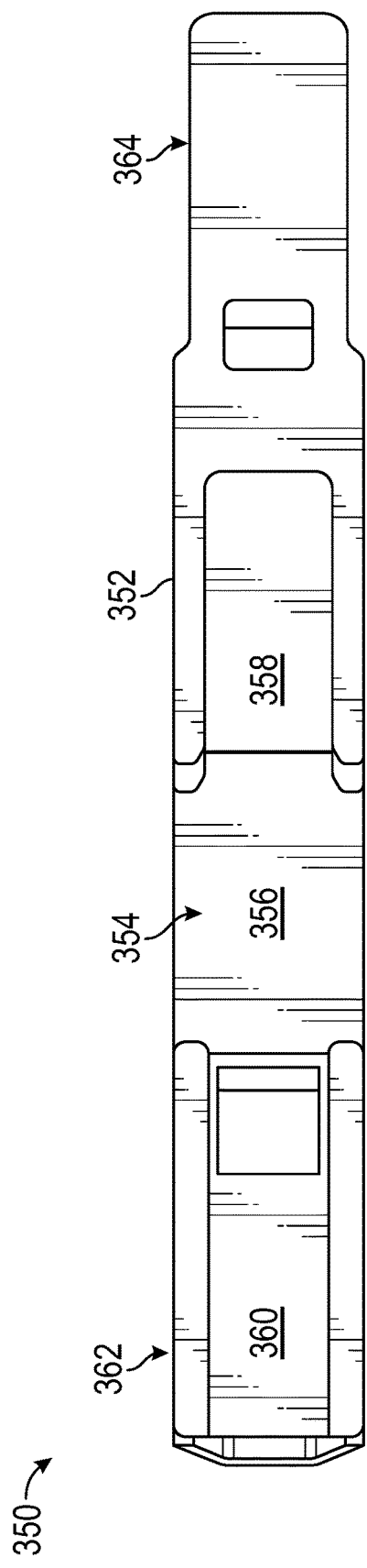

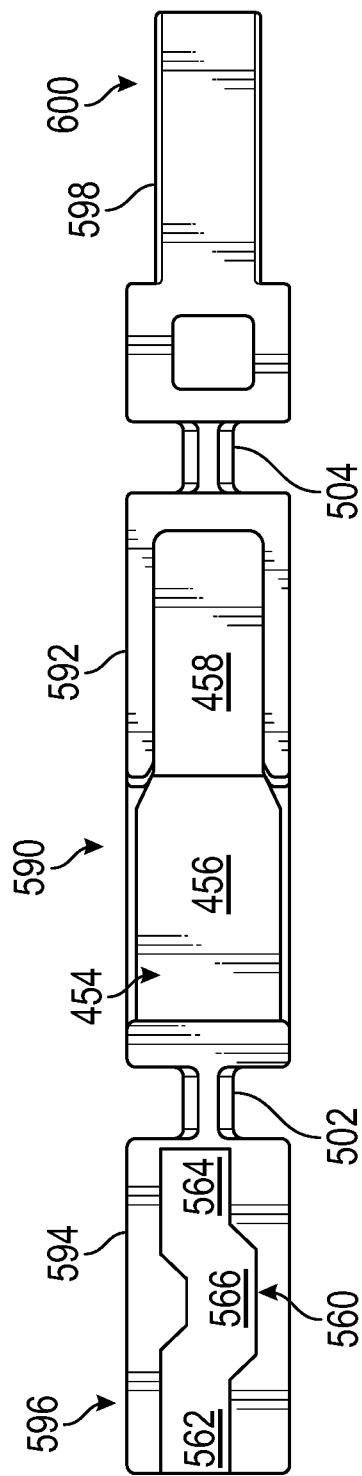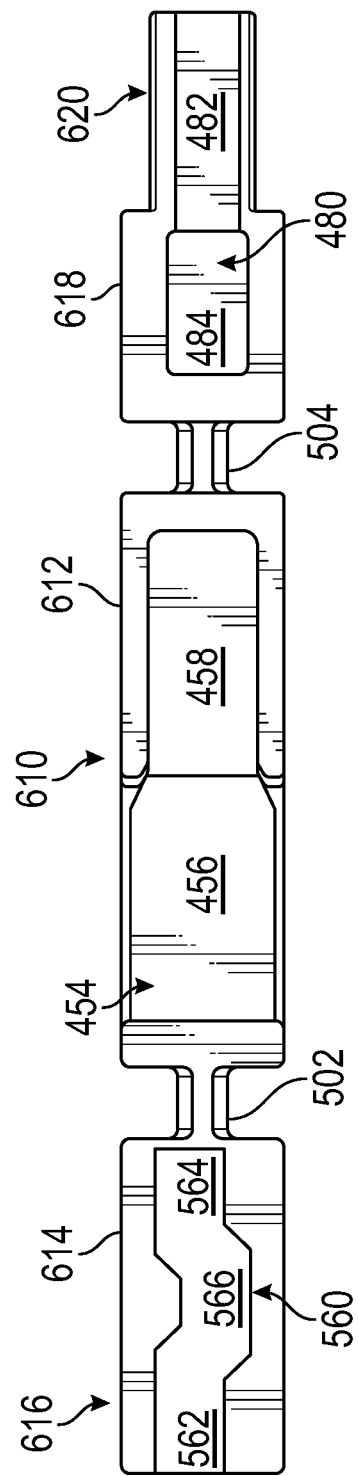

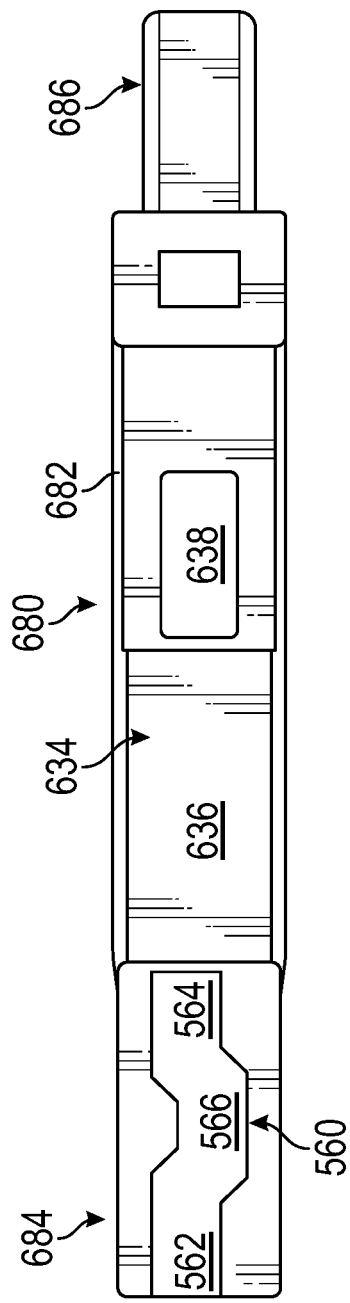
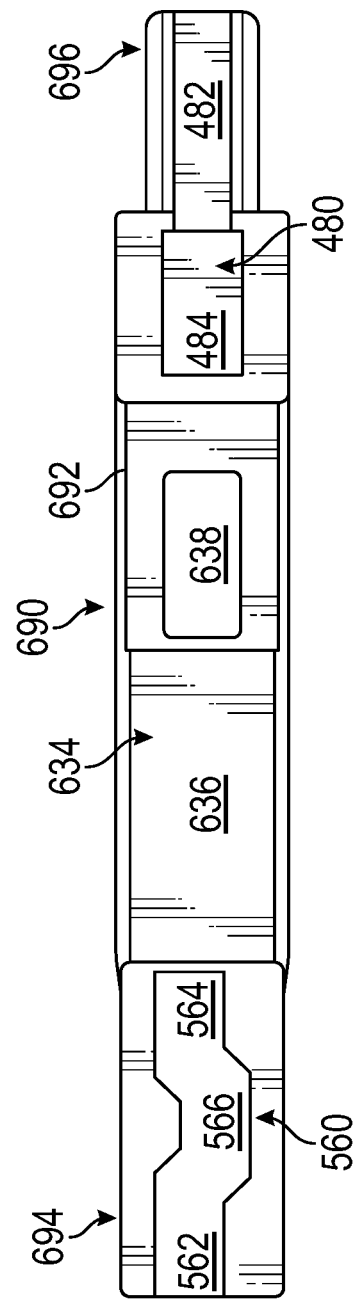
FIG. 22
FIG. 23

MOUNTING STRUCTURES FOR COMPONENTS OF INTRAVASCULAR DEVICES

CROSS-REFERENCE TO RELATED APPLICATIONS

The present application is a continuation of U.S. patent application Ser. No. 14/014,868, filed Aug. 30, 2013, now U.S. Pat. No. 9,974,446, which claims priority to and the benefit of U.S. Provisional Patent Application No. 61/695,970, filed Aug. 31, 2012, each of which is hereby incorporated by reference in its entirety.

TECHNICAL FIELD

The present disclosure relates to intravascular devices, systems, and methods. In some embodiments, the intravascular devices are guide wires that include a mounting structure for one or more sensing components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the limited space available for the core wire after accounting for the space needed for the conductors or communication lines of the electronic component(s), the stiffness and size of the rigid housing containing the electronic component(s), and/or other limitations associated with providing the functionality of the electronic components in the limited space available within a guide wire.

Accordingly, there remains a need for improved intravascular devices, systems, and methods that include a mounting structure for one or more electronic, optical, or electro-optical sensing components.

SUMMARY

Embodiments of the present disclosure are directed to intravascular devices, systems, and methods.

In one embodiment, a guide wire is provided. The guide wire comprises a first flexible element; a distal core extending within the first flexible element; a mounting structure fixedly secured to the distal core, the mounting structure comprising a plurality of material layers secured to one another, wherein the plurality of material layers define a recess sized and shaped to receive a pressure sensing component; a pressure sensing component mounted to the mounting structure; a proximal core fixedly attached to the mounting structure and extending proximally from the mounting structure; and at least one conductor having a proximal section and a distal section, wherein the distal section of the at least one conductor is coupled to the pressure sensing component and the proximal section of the at least one conductor is coupled to at least one connector; wherein the first flexible element and the mounting structure have an outer diameter of 0.018" or less.

In another embodiment, a mounting structure for use within a distal portion of a guide wire having an outer diameter of 0.018" or less is provided. The mounting structure includes a plurality of material layers secured to one another, wherein the plurality of material layers define a first recess sized and shaped to receive a pressure sensing component and a second recess sized and shaped to receive a portion of a core of the guide wire.

In some instances, the plurality of material layers of the mounting structure comprises at least six layers. In some embodiments, the plurality of material layers are each formed of the same material. In that regard, in some instances the material is nickel cobalt. Further, in some implementations each of the plurality of material layers has the same thickness. For example, in some instances the thickness of each of the plurality of material layers is between about 0.01 mm and about 0.025 mm. In some embodiments, the mounting structure includes a proximal portion, a central portion, and a distal portion. The proximal portion is separated from the central portion by a proximal bridge having a reduced outer profile dimension relative to the proximal and central portions and the central portion is separated from the distal portion by a distal bridge having a reduced outer profile dimension relative to the central and distal portions. In some instances, each of the proximal portion, central portion, and distal portion have an outer profile dimension between about 0.125 mm and about 0.400 mm and each of the proximal bridge and the distal bridge have an outer profile dimension between 0.075 mm and about 0.125 mm.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3 is a diagrammatic perspective view of a mounting structure according to an embodiment of the present disclosure.

FIG. 4 is a diagrammatic proximal end view of the mounting structure of FIG. 3.

FIG. 5 is a diagrammatic top view of a mounting structure according to another embodiment of the present disclosure.

FIG. 17 is a diagrammatic top view of a mounting structure according to another embodiment of the present disclosure.

FIG. 18 is a diagrammatic top view of a mounting structure according to another embodiment of the present disclosure.

FIG. 22 is a diagrammatic top view of a mounting structure according to another embodiment of the present disclosure.

FIG. 23 is a diagrammatic top view of a mounting structure according to another embodiment of the present disclosure.

DETAILED DESCRIPTION

Figure 1:
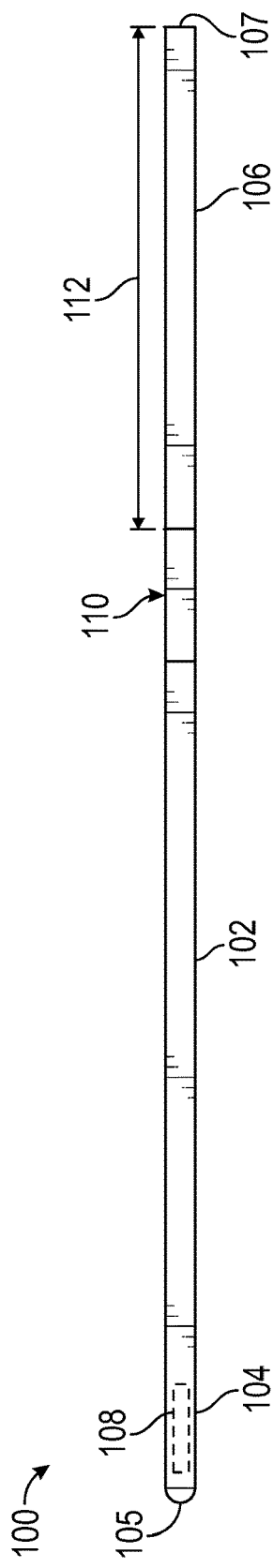
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal end 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. Some specific embodiments of electrical connectors in accordance with the present disclosure are discussed below in the context of FIGS. 5-11. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Further, in some embodiments the connector 110 provides both electrical and optical connections to both electrical conductor(s) and optical communication pathway(s) coupled to the component 108. In that regard, it should again be noted that component 108 is comprised of a plurality of elements in some instances. In some instances, the connector 110 is configured to provide a physical connection to another device, either directly or indirectly. In other instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. Generally, any number of electrical conductors, optical pathways, and/or combinations thereof can extend along the length of the flexible elongate member 102 between the connector 110 and the component 108. In some instances, between one and ten electrical conductors and/or optical pathways extend along the length of the flexible elongate member 102 between the connector 110 and the component 108. For the sake of clarity and simplicity, the embodiments of the present disclosure described below include three electrical conductors. However, it is understood that the total number of communication pathways and/or the number of electrical conductors and/or optical pathways is different in other embodiments. More specifically, the number of communication pathways and the number of electrical conductors and optical pathways extending along the length of the flexible elongate member 102 is determined by the desired functionality of the component 108 and the corresponding elements that define component 108 to provide such functionality.

Figure 2:
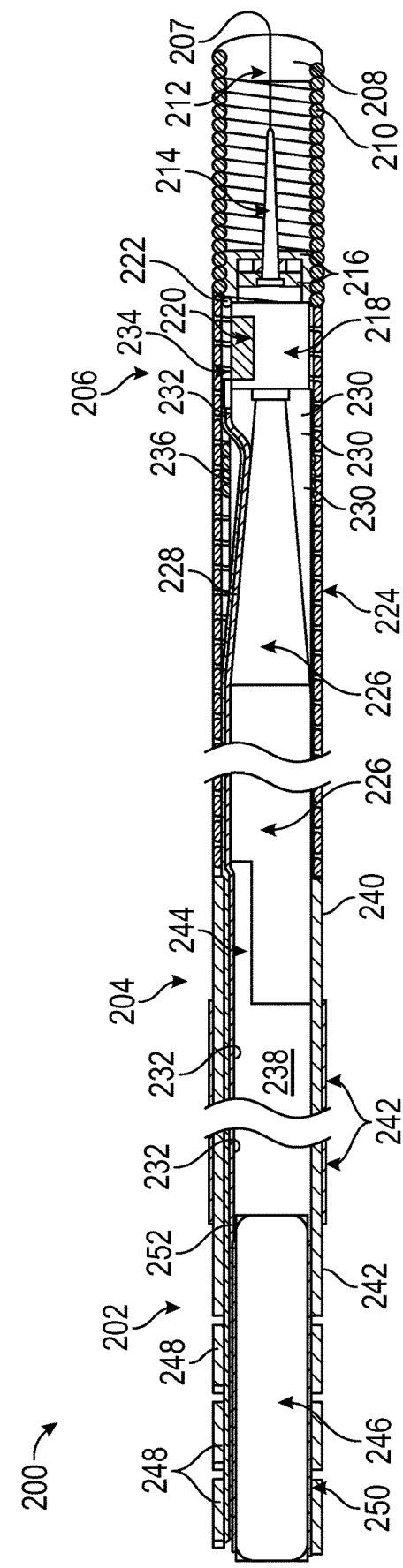
FIG. 2 is diagrammatic cross-sectional side view of an intravascular device according to an embodiment of the present disclosure.

Referring now to FIG. 2, shown therein is a cross-sectional side view of an intravascular device 200 according to an embodiment of the present disclosure. As shown, the intravascular device 200 includes a proximal portion 202, a middle portion 204, and a distal portion 206. Generally, the proximal portion 202 is configured to be positioned outside of a patient, while the distal portion 206 and a majority of the middle portion 204 are configured to be inserted into the patient, including within human vasculature. In that regard, the middle and distal portion 204 have an outer diameter between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). In the illustrated embodiment of FIG. 2, the intravascular device 200 has an outer diameter of 0.014" (0.3556 mm).

As shown, the distal portion 206 of the intravascular device 200 has a distal tip 207 defined by an element 208. In the illustrated embodiment, the distal tip 207 has a rounded profile. In some instances, the element 208 is radiopaque such that the distal tip 207 is identifiable under x-ray, fluoroscopy, and/or other imaging modalities when positioned within a patient. In some particular instances, the element 208 is solder secured to a flexible element 210 and/or a flattened tip core 212. In that regard, in some instances the flexible element 210 is a coil spring. The flattened tip core 212 extends distally from a distal core 214. As shown, the distal core 214 tapers to a narrow profile as it extends distally towards the distal tip 207. In some instances, the distal core 214 is formed of a stainless steel that has been ground down have the desired tapered profile. In some instances, the distal core 214 or at least a portion thereof is flattened to define an atraumatic tip to the intravascular device 200. In some particular instances, the distal core 214 is formed of high tensile strength 304V stainless steel. In an alternative embodiment, the distal core 214 is formed by wrapping a stainless steel shaping ribbon around a nitinol core. Solder points 216 secure the distal core 214 to a mounting structure 218. The mounting structure 218 is configured to receive and securely hold a component 220. In that regard, the component 220 is one or more of an electronic component, an optical component, and/or electro-optical component. For example, without limitation, the component 220 may be one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof.

The mounting structure 218 is fixedly secured within the distal portion 206 of the intravascular device 200. As will be discussed below in the context of the exemplary embodiments of FIGS. 3-23, the mounting structure 218 may be fixedly secured to one or more cores (e.g., a single core running along the length of the mounting structure; a proximal core; a distal core; both a proximal core and a distal core) and/or a hypotube or other structure surrounding at least a portion of the mounting structure. In the illustrated embodiment, the mounting structure is disposed within flexible element 210 and/or a flexible element 224 and secured in place by an adhesive or solder 222. In some instances, the flexible element 224 is ribbon coil covered with a polymer coating. For example, in one embodiment the flexible element 224 is a stainless steel ribbon wire coil coated with polyethylene terephthalate (PET). In another embodiment, the flexible element is a polyimide tubing that has a ribbon wire coil embedded therein. For example, in some instances a polyimide or Pebax tubing with embedded coil is utilized for flexible element 224. In some particular embodiments, the ribbon wire coil is embedded to an inner diameter of the polyimide tubing. In some instances, an opening is created in the tubing to allow the surrounding ambient pressure to reach a pressure-sensing implementation of component 220. Accordingly, in some implementations the pitch and/or spacing of an embedded ribbon coil has adequate spacing such that an opening can be created solely through the surrounding polymer portions of the tubing (i.e., not through the coil) and still provide sufficient access to facilitate accurate pressure readings. The adhesive 222 is utilized to secure the mounting structure 218 to the flexible element 210 and/or the flexible element 224 in some implementations. Accordingly, in some instances the adhesive is urethane acrylate, cyanoacrylate, silicone, epoxy, and/or combinations thereof.

The mounting structure 218 is also secured to a core 226 that extends proximally from the mounting structure towards the middle portion 204 of the intravascular device 200. In that regard, a distal portion 228 of the core 226 tapers as it extends distally towards mounting structure 218. A distal end of the distal portion 228 of the core 226 is fixedly secured to the mounting structure 218. In some instances, the distal end of the core 226 is soldered to the mounting structure 218. As shown, adhesive 230 surrounds at least a portion of the distal portion 228 of the core 226. In some instances, the adhesive 230 is the adhesive 222 used to secure the mounting structure 218 to the flexible element 210 and/or flexible element 224. In other instances, adhesive 230 is a different type of adhesive than adhesive 222. In one particular embodiment, adhesive or solder 222 is particularly suited to secure the mounting structure to flexible element 210, while adhesive 230 is particularly suited to secure the mounting structure to flexible element 224.

A communication cable 232 extends along the length of the intravascular device 200 from the proximal portion 202 to the distal portion 206. In that regard, the distal end of the communication cable 232 is coupled to the component 220 at junction 234. The type of communication cable utilized is dependent on the type of electronic, optical, and/or electro-optical components that make up the component 220. In that regard, the communication cable 232 may include one or more of an electrical conductor, an optical fiber, and/or combinations thereof. Appropriate connections are utilized at the junction 234 based on the type of communication lines included within communication cable 232. For example, electrical connections are soldered in some instances, while optical connections pass through an optical connector in some instances. In some embodiments, the communication cable 232 is a trifilar structure. Further, it is understood that all and/or portions of each of the proximal, middle, and/or distal portions 202, 204, 206 of the intravascular device 200 may have cross-sectional profiles as shown in FIGS. 2-5 of U.S. Provisional Patent Application No. 61/665,697 filed on Jun. 28, 2012, which is hereby incorporated by reference in its entirety.

Further, in some embodiments, the proximal portion 202 and/or the distal portion 206 incorporate spiral ribbon tubing as disclosed in U.S. Provisional Patent Application No. 61/665,697 filed on Jun. 28, 2012. In some instances, the use of such spiral ribbon tubing allows a further increase in the available lumen space within the device. For example, in some instances use of a spiral ribbon tubing having a wall thickness between about 0.001" and about 0.002" facilitates the use of a core wire having an outer diameter of at least 0.0095" within a 0.014" outer diameter guide wire using a trifilar with circular cross-sectional conductor profiles. The size of the core wire can be further increased to at least 0.010" by using a trifilar with the flattened oblong cross-section conductor profiles. The availability to use a core wire having an increased diameter allows the use of materials having a lower modulus of elasticity than a standard stainless steel core wire (e.g., superelastic materials such as Nitinol or NiTiCo are utilized in some instances) without adversely affecting the handling performance or structural integrity of the guide wire and, in many instances, provides improvement to the handling performance of the guide wire, especially when a superelastic material with an increased core diameter (e.g., a core diameter of 0.0075" or greater) is utilized within the distal portion 206.

The distal portion 206 of the intravascular device 200 also optionally includes at least one imaging marker 236. In that regard, the imaging marker 236 is configured to be identifiable using an external imaging modality, such as x-ray, fluoroscopy, angiograph, CT scan, MRI, or otherwise, when the distal portion 206 of the intravascular device 200 is positioned within a patient. In the illustrated embodiment, the imaging marker 236 is a radiopaque coil positioned around the tapered distal portion 228 of the core 226. Visualization of the imaging marker 236 during a procedure can give the medical personnel an indication of the size of a lesion or region of interest within the patient. To that end, the imaging marker 236 can have a known length (e.g., 0.5 cm or 1.0 cm) and/or be spaced from the element 208 by a known distance (e.g., 3.0 cm) such that visualization of the imaging marker 236 and/or the element 208 along with the anatomical structure allows a user to estimate the size or length of a region of interest of the anatomical structure. It is understood that a plurality of imaging markers 236 are utilized in some instances. In that regard, in some instances the imaging markers 236 are spaced a known distance from one another to further facilitate measuring the size or length of the region of interest.

In some instances, a proximal portion of the core 226 is secured to a core 238 that extends through the middle portion 204 of the intravascular device. In that regard, the transition between the core 226 and the core 238 may occur within the distal portion 206, within the middle portion 204, and/or at the transition between the distal portion 206 and the middle portion 204. For example, in the illustrated embodiment the transition between core 226 and core 238 occurs in the vicinity of a transition between the flexible element 224 and a flexible element 240. The flexible element 240 in the illustrated embodiment is a hypotube. In some particular instances, the flexible element is a stainless steel hypotube. Further, in the illustrated embodiment a portion of the flexible element 240 is covered with a coating 242. In that regard, the coating 242 is a hydrophobic coating in some instances. In some embodiments, the coating 242 is a polytetrafluoroethylene (PTFE) coating. In some implementations, the flexible element 240 is configured to provide more structural support than the flexible element 224. For example, in some instances the flexible 240 provides increased pushability and torqueability. Further, in some instances, primary functions of the flexible element 224 include providing a constant outer diameter for device delivery and to act as a substrate for lubricious coatings (e.g., hydrophilic coatings in some instances). In some instances, the flexible element 224 provides minimal structural support and/or torqueability, while the distal core 226 provides the desired structural support and torque response for the working section of the intravascular device 200 that enters vasculature.

The proximal portion of core 226 is fixedly secured to the distal portion of core 238. In that regard, any suitable technique for securing the cores 226, 238 to one another may be used. In some embodiments, at least one of the cores 226, 238 includes a plunge grind or other structural modification that is utilized to couple the cores together. In some instances, the cores 226, 238 are soldered together. In some instances, an adhesive is utilized to secure the cores 226, 238 together. In some embodiments, combinations of structural interfaces, soldering, and/or adhesives are utilized to secure the cores 226, 238 together. In other instances, the core 226 is not fixedly secured to core 238. For example, in some instances, the core 226 and the core 246 are fixedly secured to the hypotube 240 and the core 238 is positioned between the cores 226 and 246, which maintains the position of the core 238 between cores 226 and 246.

In some embodiments, the core 238 is formed of a different material than the core 226. For example, in some instances the core 226 is formed of nitinol and the core 238 is formed of stainless steel. In other instances, the core 238 and the core 226 are formed of the same material. In some instances the core 238 has a different profile than the core 226, such as a larger or smaller diameter and/or a non-circular cross-sectional profile. For example, in some instances the core 238 has a D-shaped cross-sectional profile. In that regard, a D-shaped cross-sectional profile has some advantages in the context of an intravascular device 200 that includes one or more electronic, optical, or electro-optical component in that it provides a natural space to run any necessary communication cables while providing increased strength than a full diameter core.

In some instances, a proximal portion of the core 238 is secured to a core 246 that extends through at least a portion of the proximal portion 202 of the intravascular device 200. In that regard, the transition between the core 238 and the core 246 may occur within the proximal portion 202, within the middle portion 204, and/or at the transition between the proximal portion 202 and the middle portion 204. For example, in the illustrated embodiment the transition between core 238 and core 246 is positioned distal of a plurality of conducting bands 248. In that regard, in some instances the conductive bands 248 are portions of a hypotube. Proximal portions of the communication cable 232 are coupled to the conductive bands 248. In that regard, in some instances each of the conductive bands is associated with a corresponding communication line of the communication cable 232. For example, in embodiments where the communication cable 232 consists of a trifilar, each of the three conductive bands 248 are connected to one of the conductors of the trifilar, for example by soldering each of the conductive bands to the respective conductor. Where the communication cable 232 includes optical communication line(s), the proximal portion 202 of the intravascular device 200 includes an optical connector in addition to or instead of one or more of the conductive bands 248. An insulating layer or sleeve 250 separates the conductive bands 248 from the core 246. In some instances, the insulating layer 250 is formed of polyimide.

As noted above, the proximal portion of core 238 is fixedly secured to the distal portion of core 246. In that regard, any suitable technique for securing the cores 238, 246 to one another may be used. In some embodiments, at least one of the cores includes a structural feature that is utilized to couple the cores together. In the illustrated embodiment, the core 238 includes an extension 252 that extends around a distal portion of the core 246. In some instances, the cores 238, 246 are soldered together. In some instances, an adhesive is utilized to secure the cores 238, 246 together. In some embodiments, combinations of structural interfaces, soldering, and/or adhesives are utilized to secure the cores 238, 246 together. In other instances, the core 226 is not fixedly secured to core 238. For example, in some instances and as noted above, the core 226 and the core 246 are fixedly secured to the hypotube 240 and the core 238 is positioned between the cores 226 and 246, which maintains the position of the core 238 between cores 226 and 246. In some embodiments, the core 246 is formed of a different material than the core 238. For example, in some instances the core 246 is formed of Nitinol and/or NiTiCo (nickel-titanium-cobalt alloy) and the core 238 is formed of stainless steel. In that regard, by utilizing a nitinol core within the conductive bands 248 instead of a stainless steel the likelihood of kinking is greatly reduced because of the increased flexibility of the nitinol core compared to a stainless steel core. In other instances, the core 238 and the core 246 are formed of the same material. In some instances the core 238 has a different profile than the core 246, such as a larger or smaller diameter and/or a non-circular cross-sectional profile.

Referring now to FIGS. 3-23, shown therein are various embodiments of mounting structures for use within intravascular devices. In some embodiments, the mounting structures of the present disclosure are sized and shaped for use within guide wires having a diameter of 0.018" or 0.014". Referring initially to FIGS. 3 and 4, shown therein is a mounting structure 300. As will be discussed below, mounting structure 300 is configured for use with a core that extends along the length of the mounting structure. Accordingly, in some embodiments where the mounting structure 300 is utilized as mounting structure 218 of intravascular device 200 discussed above, distal core 214 and proximal core 226 are defined by a single core that extends along and/or through mounting structure 300.

As shown, mounting structure 300 includes a body 302 having various structural features to facilitate interfacing with other components of the intravascular device. For example, the body 302 includes a recess 304 configured to receive a sensing component of the intravascular device. In the illustrated embodiment, the recess 304 is particularly suited for use with a pressure sensing element. In that regard, the recess 304 includes a portion 306 and a portion 308. Portion 306 has a wider profile than portion 308. Accordingly, in some implementations portion 306 is sized and shaped to receive a main body of a pressure sensing element, while portion 308 is sized and shaped to receive a portion of an active portion of the pressure sensing element (e.g., a cantilevered structure including a pressure-sensing diaphragm). In some instances, the portion 308 is recessed a greater distance relative to an upper surface (as viewed in FIG. 3) of the body 302 than portion 306. Such an arrangement allows the diaphragm or other pressure sensing portion to be positioned face up and/or face down within the recess 308. In other instances, the portions 306 and 308 have the same depth relative to an upper surface of the body 302. The body 302 also includes a recess 310 proximal of the recess 304 and adjacent a proximal portion 312 of the body. In some instances, recess 310 is sized and shaped to facilitate connection of conductors to a sensing element mounted within recess 304. For example, in some implementations conductors of a trifilar are connected to a pressure sensing element seated within recess 304 by positioning the conductors within recess 310. The body 302 includes a distal portion 314 opposite proximal portion 312 that is configured to interface with components of the distal tip of the guide wire, such as a distal core, distal coil, and/or other features.

As best seen in FIG. 4, the body 302 defines a recess or opening 316 that extends along the length of the mounting structure 300 between the proximal portion 312 and the distal portion 314. In that regard, the recess or opening 316 is sized and shaped to interface with a core wire. In some instances, the core wire is positioned within the recess/opening 316 and then fixedly secured into place using solder, adhesive, and/or other suitable techniques. As also shown in FIG. 4, the body 302 of the mounting structure 300 has a maximum height 318 and a maximum width 320. In some embodiments, the maximum height 318 is between about 0.125 mm and about 0.400 mm, with some 0.014" outer diameter devices having a maximum height of approximately 0.200 mm and some 0.018" outer diameter devices having a maximum height of approximately 0.300 mm. In some embodiments, the maximum width 320 is between about 0.28 mm and about 0.50 mm, with some 0.014" outer diameter devices having a maximum width of approximately 0.295 mm and some 0.018" outer diameter devices having a maximum height of approximately 0.450 mm. In the illustrated embodiment, the sides of the mounting structure 300 have an overall rounded or arcuate profile. In that regard, the radius or rate of curvature of the rounded/arcuate sides is determined based on the desired outer diameter (e.g., 0.014", 0.018", etc.) of the guide wire into which the mounting structure 300 will be incorporated. As discussed below, the rounded/arcuate shape of the body 302 is defined in stepwise manner by varying the width of adjacent material layers of a plurality of layers that make of the body 302 in some instances. As shown in FIG. 3, the body 302 also has a length 322 between its proximal and distal ends. In some embodiments, the length 322 is between about 1.5 mm and about 2.2 mm.

As shown in FIG. 4, the body 302 is made up of a plurality of material layers. In the illustrated embodiment, the body 302 includes layers 330, 331, 332, 333, 334, 335, 336, 337, and 338. Generally, structures in accordance with the present disclosure may use between two and fifty material layers to define a desired three-dimensional structural layout. However, most structures for use within guide wires having an outer diameter of 0.014" will utilize between six and twelve material layers. In that regard, layer 330 defines a bottom surface of the body 302, layer 338 defines an upper surface of the body, and layers 331, 332, 333, 334, 335, 336, and 337 are intermediate layers therebetween. In the illustrated embodiment, each of the layers 330, 331, 332, 333, 334, 335, 336, 337, and 338 is a plate-like structure (i.e., having parallel upper and lower surfaces with a generally constant thickness). In some embodiments, each layer has thickness (i.e., measured in the direction of height 318 of the body 302 between an upper boundary of the layer and a lower boundary of the layer) between about 0.01 mm and about 0.025 mm. In some embodiments, at least layers 330, 331, 332, 333, 334, 336, 337, and 338 each have a common thickness. Further, while layer 335 is identified as a single layer having an increased thickness relative to the other layers 330, 331, 332, 333, 334, 336, 337, and 338 in FIG. 4, it is understood that in some instances layer 335 is comprised of a plurality of layers having the common thickness that are coupled together to form the collective layer 335.

By precisely defining the geometry of each layer 330, 331, 332, 333, 334, 335, 336, 337, and 338 and then arranging the layers together, the resulting body 302 can define very precise structures. For example, the boundaries of recess 304 can be precisely defined to match those of a pressure sensor to be mounted within the recess. In that regard, the illustrated embodiment of FIG. 3 shows a tapered transition consisting of angled surfaces extending between portion 306 of recess 304 and portion 308. In some instances, the tapered transition is defined by layers 337 and 338, while the surface of portion 306 is defined by layer 336. To that end, in some embodiments manufacturing techniques are utilized that allow for micron-level precision in the manufacturing of each layer and, therefore, result in micron-level precision in the resulting structure of the body 302. This increased precision of the body 302 allows for the structural support required to limit the transfer of external forces (e.g., from curvature of the intravascular device passing through a vessel) to the sensing element, which can cause errors in the resulting measurements of the sensing element, to be achieved through a minimum sized mounting structure. As a result of the reduced size of the mounting structure 300 achievable using the multiple layer arrangements of the present disclosure, the overall flexibility of the distal portion of the intravascular device can be increased, which leads to better maneuverability and control of the intravascular device.

In some instances, the mounting structure 300 and other mounting structures of the present application are manufactured using one or more of the following steps. As an initial step, a structural design for the body 302 of the mounting structure is created. In that regard, the structural design of the body 302 takes into account such considerations as guide wire diameter, sensing element properties (e.g., type, size, shape, communication lines needed, etc.), desired flexibility of the guide wire, core wire interface(s), hypotube characteristics, desired stiffness of mounting structure, and/or features related to the mounting structure and/or related components of the guide wire. Based on the structural design, the body 302 is separated into a plurality of discrete material layers. In that regard, each layer has a defined two-dimensional profile based on the overall structural design. The thickness of each of the plurality of layers is determined based on the overall structural design. As discussed above, the plurality of layers may have a common thickness, different thicknesses, and/or combinations thereof. In some instances, the thickness of each layer is between about 5 μm and about 25 μm. With the structural design separated into a plurality of layers, one or more copies of the device are laid out on a wafer. Depending on the size of the device, anywhere from tens to hundreds to thousands of device layouts can be placed on a single wafer. Photomasks are produced for each layer in some instances. With the wafer layout established and photomasks ready, a sacrificial layer (e.g., copper) is electroplated on the wafer (e.g., a ceramic wafer). As understood by those skilled in the art, the sacrificial layer is removed (e.g., etched) at the end of the fabrication process to release the created mounting structure from the wafer. With the sacrificial layer deposited, a precise thickness of photoresist is applied to the wafer. Then the appropriate photomask is placed on top of the photoresist. In that regard, it is understood that the mounting structure 300 can be formed by beginning with layer 330 and going to layer 338 or formed by beginning with layer 338 and going to layer 330. Accordingly, depending on the order of formation, the appropriate photomask is utilized. The photomask is exposed to ultraviolet light to create a pattern on the surface of the photoresist.

With the pattern formed on the photoresist, the wafer is placed into an electro-deposition cell or chamber. The electro-deposition cell or chamber causes metal ions to be deposited in accordance with the pattern. In that regard, the metal ions used is dependent on the desired metal for the resulting mounting structure. In some instances, the metal is palladium, a Nickel Cobalt alloy (e.g., 80% nickel, 20% cobalt in one embodiment), and/or other suitable metal. With the metal layer deposited, the photoresist is removed and the sacrificial material (e.g., copper) is deposited where the photoresist was removed. The sacrificial material fills any gaps between layers of the body and acts as a stable, electrically conductive structure for the formation of a subsequent layer. The deposited metal and sacrificial layer are then planarized to the desired thickness for that layer of the body. The planarization process ensures that the layer has the desired thickness, flatness, and parallel surfaces needed for formation of the mounting structure. In some embodiments, the planarization process controls such features within 2 microns. The steps of applying a photoresist, patterning using a photomask, depositing metal into the pattern, removing the photoresist, applying a sacrificial material, and planarizing is repeated for each layer of the body. In that regard, the mounting structures of the present disclosure generally have between 6 layers and 15 layers, but some embodiments may have a greater number or fewer number of layers. Once all of the layers have been formed, all of the sacrificial material is removed to define the resulting device and release it from the wafer. In some particular embodiments, the mounting structures of the present disclosure are manufactured by Microfabrica® having a place of business in Van Nuys, Calif.

Figure 6:
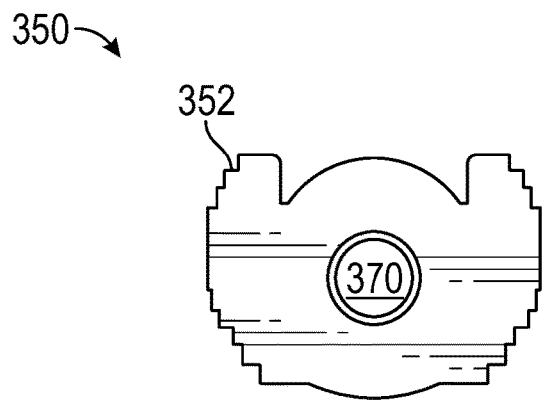
FIG. 6 is a diagrammatic proximal end view of the mounting structure of FIG. 5 shown connected to a core according to an embodiment of the present disclosure.
Figure 7:
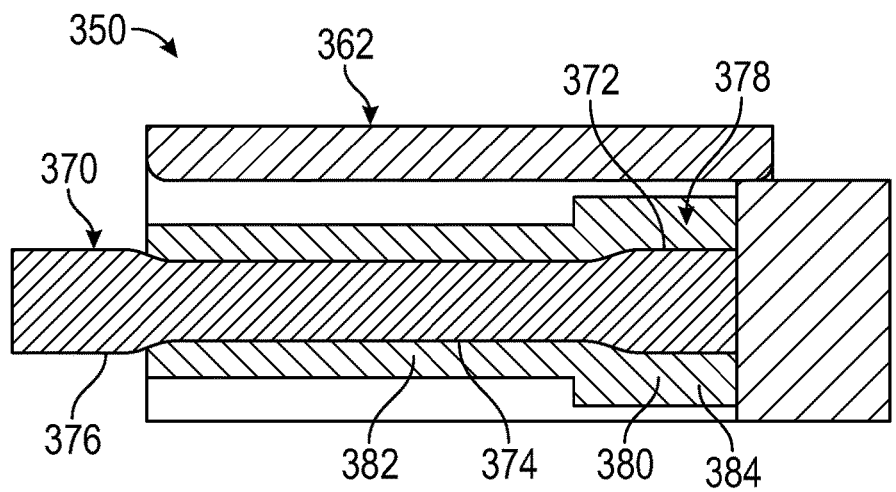
FIG. 7 is a diagrammatic partial cross-sectional side view of the mounting structure of FIGS. 5 and 6, shown connected to the core.

Referring now to FIGS. 5-7, shown therein is a mounting structure 350 according to another embodiment of the present disclosure. As will be discussed below, in contrast to mounting structure 300 that is configured for use with a core that extends along the length of the mounting structure, mounting structure 350 is configured for use with two cores, in particular a proximal core extending proximally from the mounting structure and a distal core extending distally from the mounting structure. Accordingly, in some embodiments where the mounting structure 350 is utilized as mounting structure 218 of intravascular device 200 discussed above, distal core 214 and proximal core 226 are coupled to the mounting structure 350 distally and proximally, respectively.

As shown, mounting structure 350 includes a body 352 having various structural features to facilitate interfacing with other components of the intravascular device. For example, the body 352 includes a recess 354 configured to receive a sensing component of the intravascular device. In the illustrated embodiment, the recess 354 is particularly suited for use with a pressure sensing element. In that regard, the recess 354 includes a portion 356 and a portion 358. Portion 356 has a wider profile than portion 358. Accordingly, in some implementations portion 356 is sized and shaped to receive a main body of a pressure sensing element, while portion 358 is sized and shaped to receive a portion of an active portion of the pressure sensing element (e.g., a cantilevered structure including a pressure-sensing diaphragm). In some instances, the portion 358 is recessed a greater distance relative to an upper surface (as viewed in FIGS. 5 and 6) of the body 352 than portion 356. Such an arrangement allows the diaphragm or other pressure sensing portion to be positioned face up and/or face down within the recess 358. In other instances, the portions 356 and 358 have the same depth relative to an upper surface of the body 352. The body 352 also includes a recess 360 proximal of the recess 354 and adjacent a proximal portion 362 of the body.

In some instances, recess 360 is sized and shaped to facilitate connection of conductors to a sensing element mounted within recess 354. For example, in some implementations conductors of a trifilar are connected to a pressure sensing element seated within recess 354 by positioning the conductors within and along recess 360. The body 352 includes a distal portion 364 opposite proximal portion 362 that is configured to interface with components of the distal tip of the guide wire, such as a distal core, distal coil, and/or other features.

As shown in FIGS. 6 and 7, a proximal core 370 is coupled to the proximal portion 362 of the body 352. In the illustrated embodiment, the core 372 includes a distal tip 372, a section 374 extending proximally from the distal tip 372 having a reduced diameter or outer profile relative to the distal tip (as shown in FIG. 7), and a section 376 extending proximally from section 374. As shown, section 376 has an increased diameter or outer profile relative to section 374. In some embodiments, section 376 and distal tip 372 have the same or substantially similar diameter or outer profile. In the illustrated embodiment, the core 370 includes tapered transitions between section 374 and each of the distal tip 372 and section 376. However, in other embodiments the transitions are stepped. The core 370 is secured to the body 302 via recess or opening 378 defined in the proximal portion 362 of the mounting structure 350. In that regard, the recess or opening 378 extends along the length of the mounting structure 350 distally from the proximal end of the body 352. In some embodiments, the recess or opening 378 is arranged such that a core positioned within the recess or opening 378 will be coaxially aligned with a central longitudinal axis of the mounting structure 350 and/or the guide wire into which the mounting structure is implemented. In other instances, the recess or opening is arranged such that a core positioned within the recess or opening 378 will be offset relative to a central longitudinal axis of the mounting structure 350 and/or the guide wire into which the mounting structure is implemented. In the illustrated embodiment, the opening 378 is configured such that the core 370 is offset slightly in a downward direction relative to a central longitudinal axis of the mounting structure 350 as view in FIGS. 6 and 7.

As shown in FIG. 7, the recess or opening 378 includes a portion 380 and a portion 382. Portion 382 extends distally from the proximal end of the body 302 to portion 380. As shown, portion 380 has an increased diameter or outer profile relative to the portion 382. In that regard, the recess or opening 378 and, in particular, the portions 380, 382 are sized and shaped to interface with a core wire. For example, in the illustrated embodiment portion 380 is sized and shaped to interface with the distal tip 372 of the core 370, while portion 382 is sized and shaped to allow the distal tip 372 to pass therethrough to portion 380 and also to interface with section 374 of the core once the core is seated within the recess or opening 378. In that regard, the core 370 is fixedly secured into place within the recess or opening 378 using solder 384 in some instances. In that regard, the solder 384 that fills portion 380 adheres to the distal tip 372 of the core 370 such that the distal tip and associated solder cannot pass through portion 382 of the recess or opening 378, thereby mechanically and/or chemically securing the core 370 to the mounting structure 350. Adhesive(s) and/or other suitable techniques for securing the core 370 to the body 352 are used in other instances. It is understood that the shape, size, and orientation of the recess or opening 378 can be varied to accommodate different types of cores, including different core shapes, sizes, and materials. Accordingly, for example, the recess or opening 378 may have a constant profile, one or more step-wise transitions, one or more tapered transitions, and/or other variations as appropriate. Further, it is understood that similar approaches are utilized to connect the distal core to the distal portion 364 of the body 352.

Generally, the body 352 of the mounting structure 350 has a maximum height between about 0.125 mm and about 0.400 mm, a maximum width between about 0.28 mm and about 0.50 mm, and a length between about 1.5 mm and about 2.2 mm. Further, in the illustrated embodiment, the sides of the mounting structure 350 have an overall rounded or arcuate profile, as shown in FIG. 6. In that regard, the radius or rate of curvature of the rounded/arcuate sides is determined based on the desired outer diameter (e.g., 0.014", 0.018", etc.) of the guide wire into which the mounting structure 350 will be incorporated. The rounded/arcuate shape of the body 352 is defined in step-wise manner by varying the width of adjacent material layers of a plurality of layers that make of the body 352 in some instances. In that regard, the body 352 is made up of a plurality of material layers, as discussed in detail above with respect to mounting structure 300, in some embodiments. Again, by precisely defining the geometry of each layer and then arranging the layers together, the resulting body 352 can define very precise structures configured to provide structural support and interface with other components of a guide wire. To that end, in some embodiments manufacturing techniques are utilized that allow for micron-level precision in the manufacturing of each layer (such as those described above) and, therefore, result in micron-level precision in the resulting structure of the body 352. This increased precision of the body 352 allows for the structural support required to limit the transfer of external forces (e.g., from curvature of the intravascular device passing through a vessel) to the sensing element, which can cause errors in the resulting measurements of the sensing element, to be achieved through a minimum sized mounting structure. As a result of the reduced size of the mounting structure 350 achievable using the multiple layer arrangements of the present disclosure, the overall flexibility of the distal portion of the intravascular device can be increased, which leads to better maneuverability and control of the intravascular device.

Figure 8:
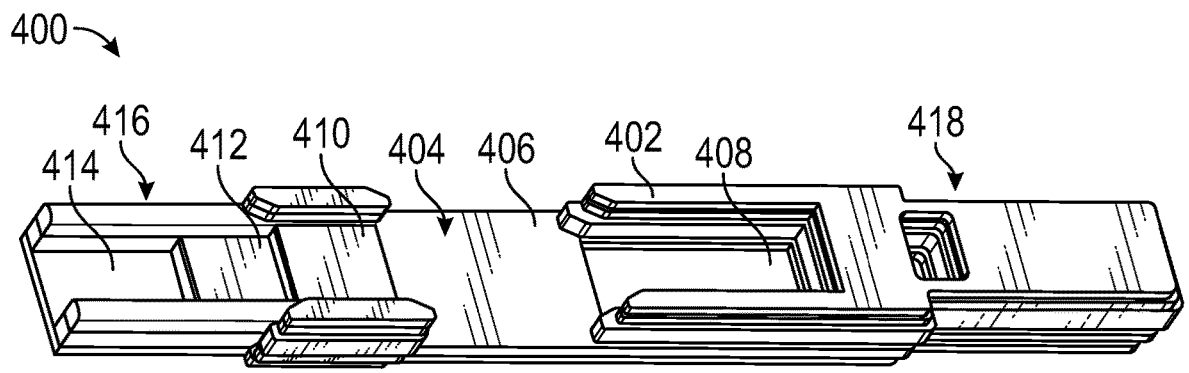
FIG. 8 is a diagrammatic perspective view of a mounting structure according to another embodiment of the present disclosure.
Figure 9:
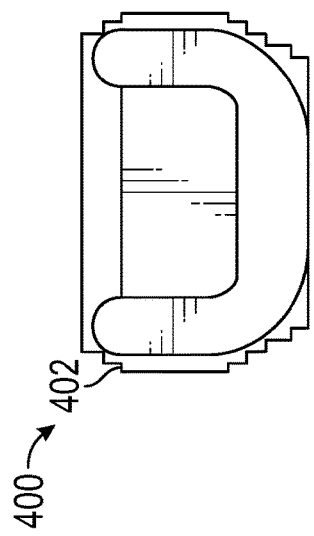
FIG. 9 is a proximal end view of the mounting structure of FIG. 8.

Referring now to FIGS. 8 and 9, shown therein is a mounting structure 400 according to another embodiment of the present disclosure. As will be discussed below, mounting structure 400 is configured to interface with and be secured to a hypotube, coil, and/or other element that at least partially surrounds the mounting structure. Accordingly, for example, in some embodiments where the mounting structure 400 is utilized as mounting structure 218 of intravascular device 200 discussed above, the mounting structure is secured to flexible element 224 and/or flexible element 210. The mounting structure 400 is also secured to a proximal core and/or distal core in some embodiments.

As shown, mounting structure 400 includes a body 402 having various structural features to facilitate interfacing with other components of the intravascular device. For example, the body 402 includes a recess 404 configured to receive a sensing component of the intravascular device. In the illustrated embodiment, the recess 404 is particularly suited for use with a pressure sensing element. In that regard, the recess 404 includes a portion 406 and a portion 408. Portion 406 has a wider profile than portion 408. Accordingly, in some implementations portion 406 is sized and shaped to receive a main body of a pressure sensing element, while portion 408 is sized and shaped to receive a portion of an active portion of the pressure sensing element (e.g., a cantilevered structure including a pressure-sensing diaphragm). In some instances, the portion 408 is recessed a greater distance relative to an upper surface (as viewed in FIG. 8) of the body 402 than portion 406. Such an arrangement allows the diaphragm or other pressure sensing portion to be positioned face up and/or face down within the recess 408. In other instances, the portions 406 and 408 have the same depth relative to an upper surface of the body 402. The body 402 also includes recesses 410, 412, and 414 proximal of the recess 404 and adjacent a proximal portion 316 of the body. As shown in FIG. 8, recess 414 is recessed a greater distance relative to the upper surface of the body 402 than recess 412, while recess 412 is recessed a greater distance relative to the upper surface of the body 402 than recess 410. In some instances, recess 414 is sized and shaped to facilitate connection of a proximal core to the body 402. In some instances, recess 412 is sized and shaped to facilitate passage of a trifilar and/or other type of communication cable from the body 402 to within a lumen of a hypotube or other tubular structural coupled to the proximal portion of the body. In some instances, recess 410 is sized and shaped to facilitate connection of conductors to a sensing element mounted within recess 404. For example, in some implementations conductors of a trifilar are connected to a pressure sensing element seated within recess 404 by positioning the conductors within and along recess 410. The body 402 includes a distal portion 418 opposite proximal portion 416 that is configured to interface with components of the distal tip of the guide wire, such as a distal core, distal coil, and/or other features.

Generally, the body 402 of the mounting structure 400 has a maximum height between about 0.125 mm and about 0.400 mm, a maximum width between about 0.28 mm and about 0.50 mm, and a length between about 1.5 mm and about 2.2 mm. Further, in the illustrated embodiment, the sides of the mounting structure 400 have an overall rounded or arcuate profile, as shown in FIG. 9. In that regard, the radius or rate of curvature of the rounded/arcuate sides is determined based on the desired outer diameter (e.g., 0.014", 0.018", etc.) of the guide wire into which the mounting structure 400 will be incorporated. The rounded/arcuate shape of the body 402 is defined in step-wise manner by varying the width of adjacent material layers of a plurality of layers that make of the body 402 in some instances. In that regard, the body 402 is made up of a plurality of material layers, as discussed in detail above with respect to mounting structure 300, in some embodiments. Again, by precisely defining the geometry of each layer and then arranging the layers together, the resulting body 402 can define very precise structures configured to provide structural support and interface with other components of a guide wire. To that end, in some embodiments manufacturing techniques are utilized that allow for micron-level precision in the manufacturing of each layer (such as those described above) and, therefore, result in micron-level precision in the resulting structure of the body 402. This increased precision of the body 402 allows for the structural support required to limit the transfer of external forces (e.g., from curvature of the intravascular device passing through a vessel) to the sensing element, which can cause errors in the resulting measurements of the sensing element, to be achieved through a minimum sized mounting structure. As a result of the reduced size of the mounting structure 400 achievable using the multiple layer arrangements of the present disclosure, the overall flexibility of the distal portion of the intravascular device can be increased, which leads to better maneuverability and control of the intravascular device.

Referring now to FIGS. 10-23, shown therein are additional exemplary embodiments of mounting structures according to present disclosure. In that regard, the mounting structures of FIGS. 10-23 incorporate many of the features discussed above with respect to mounting structures 300, 350, and 400 and may be manufactured using similar techniques. Accordingly, the following discussion focuses on the general structures of the illustrated embodiments. In that regard, common reference numerals are used across different embodiments to represent similar structural features. Further, it should be noted that the mounting structures illustrated in FIGS. 3-23 are drawn to scale and therefore, the structural arrangements of the mounting structures are to scale.

Figure 10:
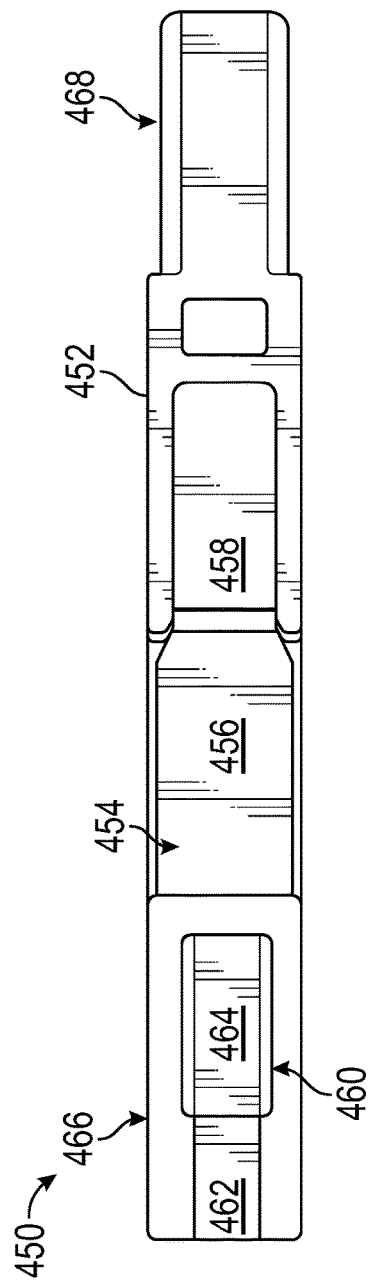
FIG. 10 is a diagrammatic top view of a mounting structure according to another embodiment of the present disclosure.

Referring now to FIG. 10, shown therein is a mounting structure 450 according to another embodiment of the present disclosure. As shown, mounting structure 450 includes a body 452 having various structural features to facilitate interfacing with other components of an intravascular device, such as a guide wire. For example, the body 452 includes a recess 454 extending from an upper surface that is configured to receive a sensing component of the intravascular device. In the illustrated embodiment, the recess 454 is particularly suited for use with a pressure sensing element. In that regard, the recess 454 includes a portion 456 and a portion 458. Portion 456 has a wider profile than portion 458. Accordingly, in some implementations portion 456 is sized and shaped to receive a main body of a pressure sensing element, while portion 458 is sized and shaped to receive a portion of an active portion of the pressure sensing element (e.g., a cantilevered structure including a pressure-sensing diaphragm). In some instances, the portion 458 is recessed a greater distance relative to an upper surface of the body 452 than portion 456. Such an arrangement allows the diaphragm or other pressure sensing portion to be positioned face up and/or face down within the recess 458. In other instances, the portions 456 and 458 have the same depth relative to an upper surface of the body 452.

The body 452 also includes a recess or opening 460 extending from a bottom surface (i.e., opposite of recess 454) that is configured to facilitate coupling of a core to the body 452. In the illustrated embodiment, the recess or opening 460 extends along the length of the mounting structure 450 distally from the proximal end of the body 452. In some embodiments, the recess or opening 460 is arranged such that a core positioned within the recess or opening 460 will be coaxially aligned with a central longitudinal axis of the mounting structure 450 and/or the guide wire into which the mounting structure is implemented. In other instances, the recess or opening is arranged such that a core positioned within the recess or opening 460 will be offset relative to a central longitudinal axis of the mounting structure 450 and/or the guide wire into which the mounting structure is implemented. As shown, the recess or opening 460 includes a portion 462 and a portion 464. Portion 462 extends distally from the proximal end of the body 452 to portion 464. As shown, portion 464 has an increased diameter or outer profile relative to the portion 462. In that regard, the recess or opening 460 and, in particular, the portions 462, 464 are sized and shaped to interface with a core wire. For example, in some instances portion 464 is sized and shaped to interface with a distal tip of the core, while portion 462 is sized and shaped to allow the distal tip to pass therethrough to portion 464. In that regard, the core is fixedly secured into place within the recess or opening 460 using solder, adhesive, and/or other suitable techniques in some instances. Accordingly, proximal portion 466 of the body 452 is configured to interface with the core and/or other components of the guide wire positioned proximal of the sensing element. The body 452 includes a distal portion 468 opposite proximal portion 466 that is configured to interface with components of the distal tip of the guide wire, such as a distal core, distal coil, and/or other features.

In some implementations for use within a guide wire having an outer diameter of 0.014", the body 452 of the mounting structure 450 has a maximum height about 0.125 mm and about 0.400 mm, a maximum width between about 0.28 mm and about 0.50 mm, and a length between about 1.5 mm and about 2.2 mm, with some particular embodiments having a maximum height of about 0.2 mm and a maximum width of about 0.295 mm. These dimensions can be scaled up or down for larger or smaller diameter guide wires. Further, in the illustrated embodiment, the sides of the mounting structure 450 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 450 will be incorporated. The rounded/arcuate shape of the body 452 is defined in step-wise manner by varying the width of adjacent material layers of a plurality of layers that make of the body 452 in some instances. In that regard, the body 452 is made up of a plurality of material layers, as discussed in detail above, in some embodiments.

Figure 11:
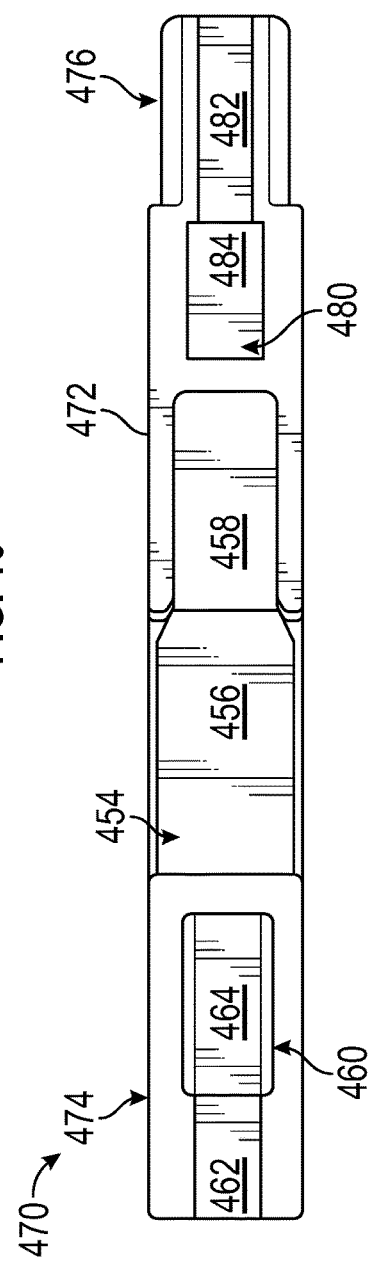
FIG. 11 is a diagrammatic top view of a mounting structure according to another embodiment of the present disclosure.

Referring now to FIG. 11, shown therein is a mounting structure 470 according to another embodiment of the present disclosure. As shown, mounting structure 470 includes a body 472 having a proximal portion 474, a distal portion 476, and various structural features to facilitate interfacing with other components of an intravascular device, such as a guide wire. For example, the body 472 includes recess 454 having portions 456 and 458 as described above. The body 472 also includes a recess or opening 460 extending from a bottom surface (i.e., opposite of recess 454) that is configured to facilitate coupling of a core to the body 472 as described above. Accordingly, proximal portion 474 of the body 472 is configured to interface with the core and/or other components of the guide wire positioned proximal of the sensing element.

The distal portion 476 of the body is configured to interface with components of the distal tip of the guide wire, such as a distal core, distal coil, and/or other features. In the illustrated embodiment, the distal portion 476 of the body 472 includes a recess or opening 480 extending from a bottom surface (i.e., opposite of recess 454) that is configured to facilitate coupling of a distal core to the body 472. As shown, the recess or opening 480 includes a portion 482 and a portion 484. Portion 482 extends proximally from the distal end of the body 472 to portion 484. As shown, portion 484 has an increased diameter or outer profile relative to the portion 482. In that regard, the recess or opening 480 and, in particular, the portions 482, 484 are sized and shaped to interface with a core wire. For example, in some instances portion 484 is sized and shaped to interface with a proximal tip of the core, while portion 482 is sized and shaped to allow the proximal tip to pass therethrough to portion 484. In that regard, the core is fixedly secured into place within the recess or opening 480 using solder, adhesive, and/or other suitable techniques in some instances.

In some implementations for use within a guide wire having an outer diameter of 0.014", the body 472 of the mounting structure 470 has a maximum height about 0.125 mm and about 0.400 mm, a maximum width between about 0.28 mm and about 0.50 mm, and a length between about 1.5 mm and about 2.2 mm, with some particular embodiments having a maximum height of about 0.2 mm and a maximum width of about 0.295 mm. These dimensions can be scaled up or down for larger or smaller diameter guide wires. Further, in the illustrated embodiment, the sides of the mounting structure 470 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 470 will be incorporated. The rounded/arcuate shape of the body 472 is defined in step-wise manner by varying the width of adjacent material layers of a plurality of layers that make of the body 472 in some instances. In that regard, the body 472 is made up of a plurality of material layers, as discussed in detail above, in some embodiments.

Figure 12:
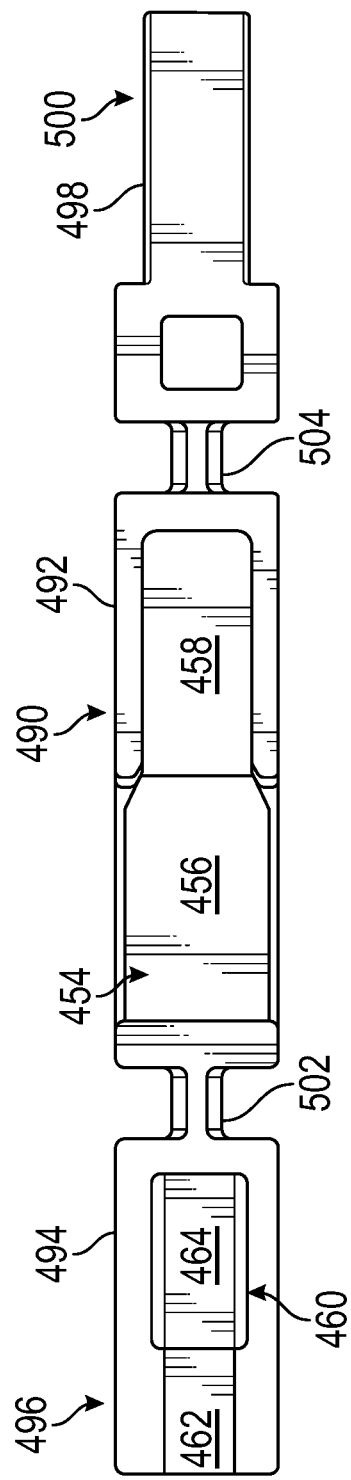
FIG. 12 is a diagrammatic top view of a mounting structure according to another embodiment of the present disclosure.

Referring now to FIG. 12, shown therein is a mounting structure 490 according to another embodiment of the present disclosure. In that regard, mounting structure 490 is similar to mounting structure 450 of FIG. 10 in many respects. However, mounting structure 490 includes three body portions separated by narrower bridges or links, instead of a single body structure. In particular, mounting structure 490 includes a central body 492, a proximal body 494 adjacent a proximal portion 496, and a distal body 498 adjacent a distal portion 500. The central body 492 includes recess 454 extending from an upper surface that is configured to receive a sensing component of the intravascular device. Further, proximal body 494 includes a recess or opening 460 extending from a bottom surface (i.e., opposite of recess 454) that is configured to facilitate coupling of a core to the mounting structure 490. Further still, the distal body 498 is configured to interface with components of the distal tip of the guide wire, such as a distal core, distal coil, and/or other features.

As shown, the proximal body 494 is connected to the central body 492 by a bridge 502, while the distal body 498 is connected to the central body 492 by a bridge 504. As shown, the bridges 502, 504 have a reduced profile relative to the proximal, central, and distal bodies 494, 492, and 496. In that regard, in some implementations the bridges 502, 504 are defined by a fewer number of material layers than the proximal, central, and distal bodies 494, 492, and 496. In some embodiments, the bridges 502, 504 have an outer diameter or other outer profile (e.g., for other geometric and non-geometric cross-sectional profiles) approximately the size of a core wire used within the intravascular device. Accordingly, in some embodiments, the bridges 502, 504 have an outer diameter or other outer profile between about 0.075 mm and about 0.125 mm. Further, in some embodiments the bridges 502, 504 have a length along the longitudinal axis of the mounting structure 490 between about 0.1 mm and about 0.5 mm. It should be noted that while bridges 502, 504 are shown as having substantially similar structural profiles, in other embodiments that outer profiles and/or lengths of the bridges 502, 504 are different. In some embodiments, the bridges 502, 504 are integrally formed with the proximal, central, and distal bodies 494, 492, and 496. In other embodiments, the bridges 502, 504 are formed separately and fixedly attached to the proximal, central, and distal bodies 494, 492, and 496.

In some implementations for use within a guide wire having an outer diameter of 0.014", the mounting structure 490 has a maximum height between about 0.125 mm and about 0.400 mm, a maximum width between about 0.28 mm and about 0.50 mm, and a length between about 0.16 mm and about 2.7 mm, with one particular embodiment having a maximum height of about 0.225 mm, a maximum width of about 0.295 mm, and a length of about 1.8 mm. These dimensions can be scaled up or down for larger or smaller diameter guide wires. Further, in the illustrated embodiment, the sides of the mounting structure 490 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 490 will be incorporated.

Figure 13:
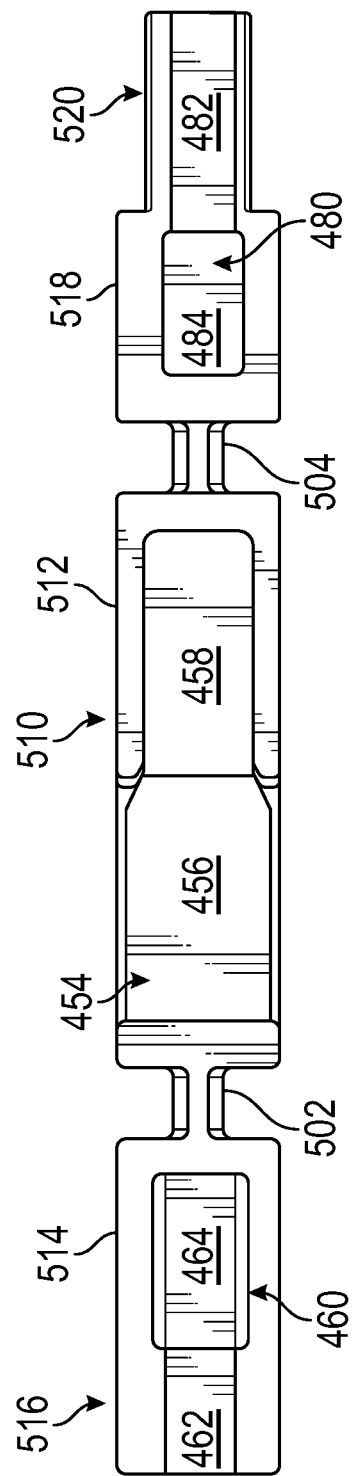
FIG. 13 is a diagrammatic top view of a mounting structure according to another embodiment of the present disclosure.

Referring now to FIG. 13, shown therein is a mounting structure 510 according to another embodiment of the present disclosure. In that regard, mounting structure 510 is similar to mounting structure 470 of FIG. 11 in many respects. However, mounting structure 510 includes three body portions separated by narrower bridges or links, instead of a single body structure. In particular, mounting structure 510 includes a central body 512, a proximal body 514 adjacent a proximal portion 516, and a distal body 518 adjacent a distal portion 520. The central body 512 includes recess 454 extending from an upper surface that is configured to receive a sensing component of the intravascular device. Further, proximal body 514 includes a recess or opening 460 extending from a bottom surface (i.e., opposite of recess 454) that is configured to facilitate coupling of a core to the mounting structure 510. Further still, the distal body 518 is configured to interface with components of the distal tip of the guide wire, such as a distal core, distal coil, and/or other features, and includes a recess or opening 480 extending from the bottom surface (i.e., opposite of recess 454). As shown, the proximal body 514 is connected to the central body 512 by a bridge 502, while the distal body 518 is connected to the central body 512 by a bridge 504.

Figure 14:
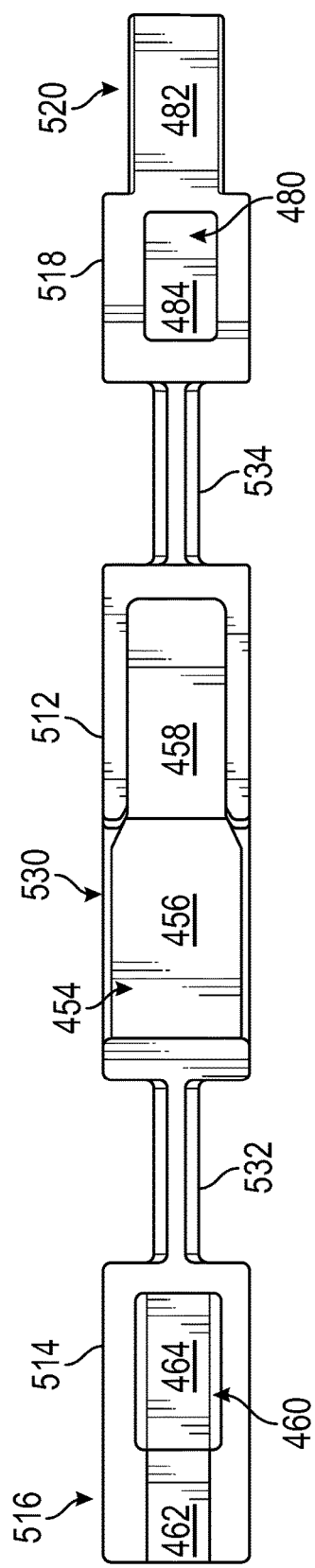
FIG. 14 is a diagrammatic top view of a mounting structure according to another embodiment of the present disclosure.

In some embodiments, the bridges 502, 504 have an outer diameter or other outer profile (e.g., for other geometric and non-geometric cross-sectional profiles) approximately the size of a core wire used within the intravascular device. Accordingly, in some embodiments, the bridges 502, 504 have an outer diameter or other outer profile between 0.075 mm and about 0.125 mm. Further, in some embodiments the bridges 502, 504 have a length along the longitudinal axis of the mounting structure between about 0.1 mm and about 0.5 mm. In that regard, the bridges 502, 504 of FIGS. 12 and 13 have a length of about 0.175 mm, whereas FIG. 14 illustrates a mounting structure 530 substantially similar to mounting structure 510, but with bridges 532, 534 having an increased length of about 0.5 mm. It should be noted that while bridges 502, 504 are shown as having substantially similar structural profiles, in other embodiments that outer profiles and/or lengths of the bridges 502, 504 are different. In some embodiments, the bridges 502, 504 are integrally formed with the proximal, central, and distal bodies 494, 492, and 496 (e.g., using a fewer number of material layers). In other embodiments, the bridges 502, 504 are formed separately and fixedly attached to the proximal, central, and distal bodies 494, 492, and 496.

In some implementations for use within a guide wire having an outer diameter of 0.014", the mounting structure 510 has a maximum height between about 0.125 mm and about 0.400 mm, a maximum width between about 0.28 mm and about 0.50 mm, and a length between about 0.16 mm and about 2.7 mm, with one particular embodiment having a maximum height of about 0.225 mm, a maximum width of about 0.295 mm, and a length of about 2.45 mm. These dimensions can be scaled up or down for larger or smaller diameter guide wires. Further, in the illustrated embodiment, the sides of the mounting structure 510 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 510 will be incorporated.

Figure 15:
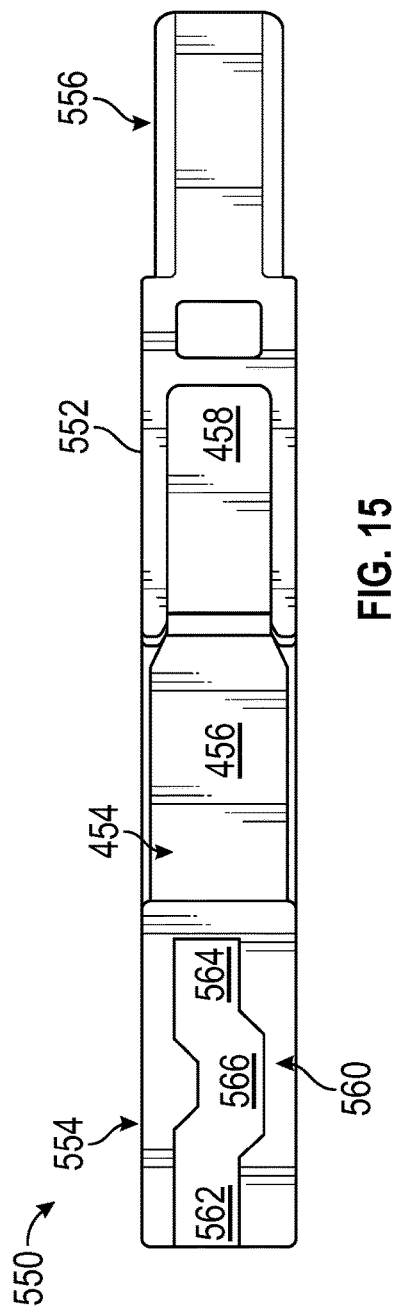
FIG. 15 is a diagrammatic top view of a mounting structure according to another embodiment of the present disclosure.

Referring now to FIG. 15, shown therein is a mounting structure 550 according to another embodiment of the present disclosure. As shown, mounting structure 550 includes a body 552, having a proximal portion 554 and a distal portion 556, that includes various structural features to facilitate interfacing with other components of an intravascular device, such as a guide wire. For example, the body 552 includes recess 454 extending from an upper surface that is configured to receive a sensing component of the intravascular device. The body 552 also includes a recess or opening 560 extending from a bottom surface (i.e., opposite of recess 454) that is configured to facilitate coupling of a core to the body 552. In the illustrated embodiment, the recess or opening 560 extends along the length of the mounting structure 550 distally from the proximal end of the body 552. In some embodiments, the recess or opening 560 is arranged such that the majority of a core positioned within the recess or opening 560 will be coaxially aligned with a central longitudinal axis of the mounting structure 550 and/or the guide wire into which the mounting structure is implemented. In other instances, the recess or opening is arranged such that a core positioned within the recess or opening 560 will be offset relative to a central longitudinal axis of the mounting structure 550 and/or the guide wire into which the mounting structure is implemented. As shown, the recess or opening 560 includes proximal and distal portions 562 and 564 that are generally aligned with one another and a central portion 566 positioned between and offset relative to the proximal and distal portions 562, 564. In that regard, the central portion 566 is in communication with the proximal and distal portion 562, 564. As shown, portion 562 extends distally from the proximal end of the body 552 to portion 566, which continues distally to portion 564. The recess or opening 560 and, in particular, the portions 562, 564, and 566 are sized and shaped to interface with a core wire. In some instances the recess or opening 560 is sized and shaped to interface with a distal tip of a proximal core. In that regard, the core is fixedly secured into place within the recess or opening 560 using solder, adhesive, and/or other suitable techniques in some instances. In that regard, the offset of central portion 566 provides a mechanical locking feature with respect to the solder, adhesive, and/or other suitable bonding technique in some instances. Further, in some instances the transitions between the proximal and distal portions 562, 564 create one or more bend(s) in the distal tip of the core to further facilitate mechanical coupling between the core and the mounting structure 550. In that regard, the illustrated slot design provides not only locking capability from a tensile force, but the jogged shape also ensures a good torsional force transmission. Accordingly, proximal portion 554 of the body 552 is configured to interface with the core and/or other components of the guide wire positioned proximal of the sensing element. The distal portion 556 of the body 552 is configured to interface with components of the distal tip of the guide wire, such as a distal core, distal coil, and/or other features.

In some implementations for use within a guide wire having an outer diameter of 0.014", the body 552 of the mounting structure 550 has a maximum height between about 0.125 mm and about 0.400 mm, a maximum width between about 0.28 mm and about 0.50 mm, and a length between about 1.5 mm and about 2.2 mm, with some particular embodiments having a maximum height of about 0.2 mm and a maximum width of about 0.295 mm. These dimensions can be scaled up or down for larger or smaller diameter guide wires. Further, in the illustrated embodiment, the sides of the mounting structure 550 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 550 will be incorporated. The rounded/arcuate shape of the body 552 is defined in stepwise manner by varying the width of adjacent material layers of a plurality of layers that make of the body 552 in some instances. In that regard, the body 552 is made up of a plurality of material layers, as discussed in detail above, in some embodiments.

Figure 16:
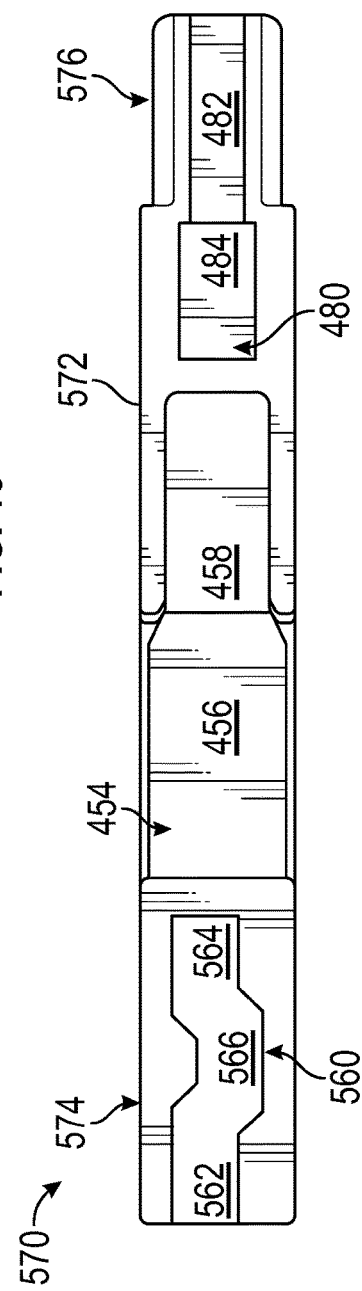
FIG. 16 is a diagrammatic top view of a mounting structure according to another embodiment of the present disclosure.

Referring now to FIG. 16, shown therein is a mounting structure 570 according to another embodiment of the present disclosure. As shown, mounting structure 570 includes a body 572 having a proximal portion 574, a distal portion 576, and various structural features to facilitate interfacing with other components of an intravascular device, such as a guide wire. For example, the body 572 includes recess 454 having portions 456 and 458 as described above. The body 572 also includes a recess or opening 560 extending from a bottom surface (i.e., opposite of recess 454) that is configured to facilitate coupling of a core to the body 572 as described above. Accordingly, proximal portion 574 of the body 572 is configured to interface with the core and/or other components of the guide wire positioned proximal of the sensing element. The distal portion 576 of the body is configured to interface with components of the distal tip of the guide wire, such as a distal core, distal coil, and/or other features. In the illustrated embodiment, the distal portion 576 of the body 572 includes a recess or opening 480 extending from a bottom surface (i.e., opposite of recess 454) that is configured to facilitate coupling of a distal core to the body 572.

In some implementations for use within a guide wire having an outer diameter of 0.014", the body 572 of the mounting structure 570 has a maximum height between about 0.125 mm and about 0.400 mm, a maximum width between about 0.28 mm and about 0.50 mm, and a length between about 1.5 mm and about 2.2 mm, with some particular embodiments having a maximum height of about 0.2 mm and a maximum width of about 0.295 mm. These dimensions can be scaled up or down for larger or smaller diameter guide wires. Further, in the illustrated embodiment, the sides of the mounting structure 570 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 450 will be incorporated. The rounded/arcuate shape of the body 572 is defined in stepwise manner by varying the width of adjacent material layers of a plurality of layers that make of the body 572 in some instances. In that regard, the body 572 is made up of a plurality of material layers, as discussed in detail above, in some embodiments.

Referring now to FIG. 17, shown therein is a mounting structure 590 according to another embodiment of the present disclosure. In that regard, mounting structure 590 is similar to mounting structure 550 of FIG. 15 in many respects. However, mounting structure 590 includes three body portions separated by narrower bridges or links, instead of a single body structure. In particular, mounting structure 590 includes a central body 592, a proximal body 594 adjacent a proximal portion 596, and a distal body 598 adjacent a distal portion 600. The central body 592 includes recess 454 extending from an upper surface that is configured to receive a sensing component of the intravascular device. Further, proximal body 594 includes a recess or opening 560 extending from a bottom surface (i.e., opposite of recess 454) that is configured to facilitate coupling of a core to the mounting structure 590. Further still, the distal body 598 is configured to interface with components of the distal tip of the guide wire, such as a distal core, distal coil, and/or other features. As shown, the proximal body 594 is connected to the central body 592 by a bridge 502, while the distal body 598 is connected to the central body 592 by a bridge 504.

In some implementations for use within a guide wire having an outer diameter of 0.014", the mounting structure 590 has a maximum height between about 0.125 mm and about 0.400 mm, a maximum width between about 0.28 mm and about 0.50 mm, and a length between about 0.16 mm and about 2.7 mm, with one particular embodiment having a maximum height of about 0.225 mm, a maximum width of about 0.295 mm, and a length of about 1.8 mm. These dimensions can be scaled up or down for larger or smaller diameter guide wires. Further, in the illustrated embodiment, the sides of the mounting structure 590 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 590 will be incorporated.

Referring now to FIG. 18, shown therein is a mounting structure 610 according to another embodiment of the present disclosure. In that regard, mounting structure 610 is similar to mounting structure 570 of FIG. 16 in many respects. However, mounting structure 610 includes three body portions separated by narrower bridges or links, instead of a single body structure. In particular, mounting structure 610 includes a central body 612, a proximal body 614 adjacent a proximal portion 616, and a distal body 618 adjacent a distal portion 620. The central body 612 includes recess 454 extending from an upper surface that is configured to receive a sensing component of the intravascular device. Further, proximal body 614 includes a recess or opening 560 extending from a bottom surface (i.e., opposite of recess 454) that is configured to facilitate coupling of a core to the mounting structure 610. Further still, the distal body 618 is configured to interface with components of the distal tip of the guide wire, such as a distal core, distal coil, and/or other features, and includes a recess or opening 480 extending from the bottom surface (i.e., opposite of recess 454). As shown, the proximal body 614 is connected to the central body 612 by a bridge 502, while the distal body 618 is connected to the central body 612 by a bridge 504.

In some implementations for use within a guide wire having an outer diameter of 0.014", the mounting structure 610 has a maximum height between about 0.125 mm and about 0.400 mm, a maximum width between about 0.28 mm and about 0.50 mm, and a length between about 0.16 mm and about 2.7 mm, with one particular embodiment having a maximum height of about 0.225 mm, a maximum width of about 0.295 mm, and a length of about 1.8 mm. These dimensions can be scaled up or down for larger or smaller diameter guide wires. Further, in the illustrated embodiment, the sides of the mounting structure 610 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 610 will be incorporated.

Figure 19:
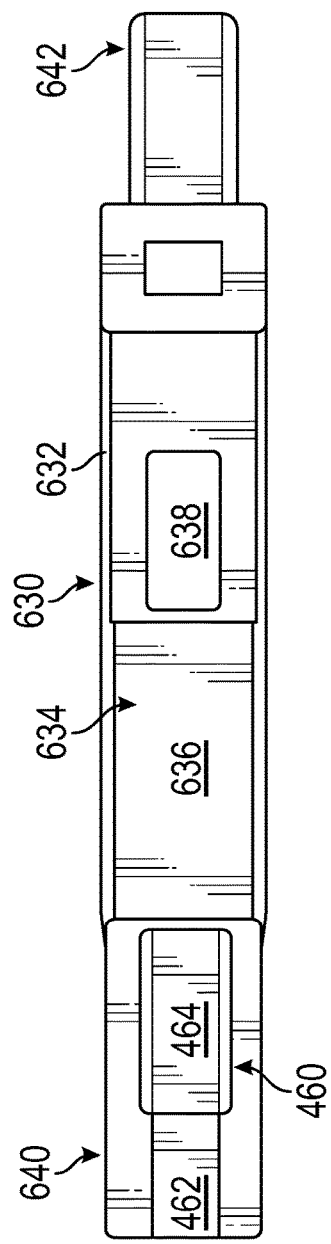
FIG. 19 is a diagrammatic top view of a mounting structure according to another embodiment of the present disclosure.

Referring now to FIGS. 19-23, shown therein are mounting structures according to additional embodiments of the present disclosure. In that regard, the embodiments of FIGS. 19-23 are similar in many respects to the embodiments of FIGS. 10, 11, 13, 15, and 16, respectively, but include an alternative recess design for interfacing with a sensing component compared to recess 454 discussed above. For example, referring more specifically to FIG. 19, shown therein is a mounting structure 630 that includes a body 632 having various structural features to facilitate interfacing with other components of an intravascular device, such as a guide wire. For example, the body 632 includes a recess 634 extending from an upper surface that is configured to receive a sensing component of the intravascular device. In the illustrated embodiment, the recess 634 is particularly suited for use with a pressure sensing element. In that regard, the recess 634 includes a planar surface portion 636 sized and shaped to receive a body of a pressure sensing element. Further, in the illustrated embodiment the body 632 includes an opening 638 extending through the body from an upper surface to a lower surface. In some instances, a diaphragm and/or other pressure sensitive portion of a pressure sensing element mounted within recess 634 is in fluid communication with the opening 638. In some particular embodiments, the diaphragm and/or other pressure sensitive portion of the pressure sensing element is positioned directly over the opening 638 (either face down (i.e., diaphragm or other pressure sensitive portion towards the opening 638) or face up (i.e., diaphragm or other pressure sensitive portion away from the opening 638)) when mounted. As shown, the body 632 includes a recess or opening 460 adjacent a proximal portion 640. The recess or opening 460 extends from a bottom surface (i.e., opposite of recess 634) that is configured to facilitate coupling of a core to the body 632. The body 632 also includes a distal portion 642 opposite proximal portion 640 that is configured to interface with components of the distal tip of the guide wire, such as a distal core, distal coil, and/or other features.

In some implementations for use within a guide wire having an outer diameter of 0.014", the body 632 of the mounting structure 630 has a maximum height between about 0.125 mm and about 0.400 mm, a maximum width between about 0.28 mm and about 0.50 mm, and a length between about 1.5 mm and about 2.2 mm, with some particular embodiments having a maximum height of about 0.2 mm and a maximum width of about 0.295 mm. These dimensions can be scaled up or down for larger or smaller diameter guide wires. Further, in the illustrated embodiment, the sides of the mounting structure 630 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 630 will be incorporated.

Figure 20:
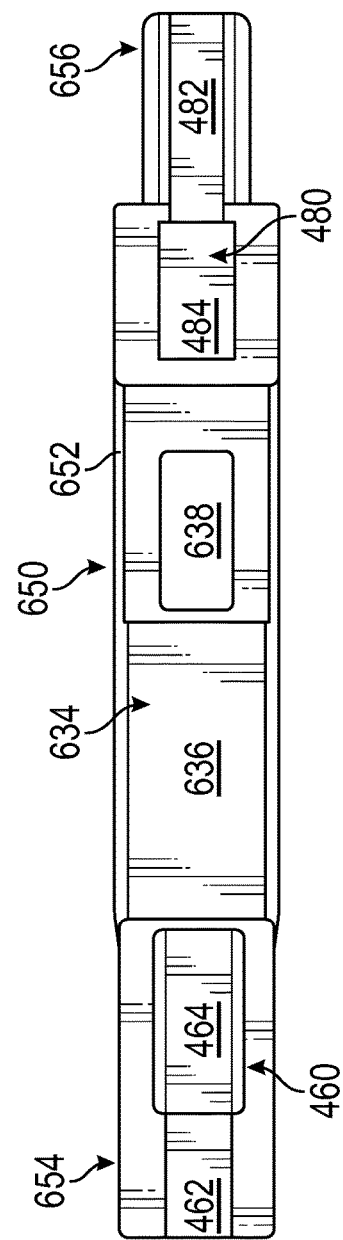
FIG. 20 is a diagrammatic top view of a mounting structure according to another embodiment of the present disclosure.

Referring now to FIG. 20, shown therein is a mounting structure 650 according to another embodiment of the present disclosure. As shown, mounting structure 650 includes a body 652 having a proximal portion 654, a distal portion 656, and various structural features to facilitate interfacing with other components of an intravascular device, such as a guide wire. For example, the body 652 includes recess 634 and opening 638 as described above. The body 652 also includes a recess or opening 460 extending from a bottom surface (i.e., opposite of recess 634) that is configured to facilitate coupling of a core to the body 652. The distal portion 656 of the body is configured to interface with components of the distal tip of the guide wire, such as a distal core, distal coil, and/or other features. In the illustrated embodiment, the distal portion 656 of the body 652 includes a recess or opening 480 extending from a bottom surface (i.e., opposite of recess 634) that is configured to facilitate coupling of a distal core to the body 472.

In some implementations for use within a guide wire having an outer diameter of 0.014", the body 652 of the mounting structure 650 has a maximum height between about 0.125 mm and about 0.400 mm, a maximum width between about 0.28 mm and about 0.50 mm, and a length between about 1.5 mm and about 2.2 mm, with some particular embodiments having a maximum height of about 0.2 mm and a maximum width of about 0.295 mm. These dimensions can be scaled up or down for larger or smaller diameter guide wires. Further, in the illustrated embodiment, the sides of the mounting structure 650 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 650 will be incorporated.

Figure 21:
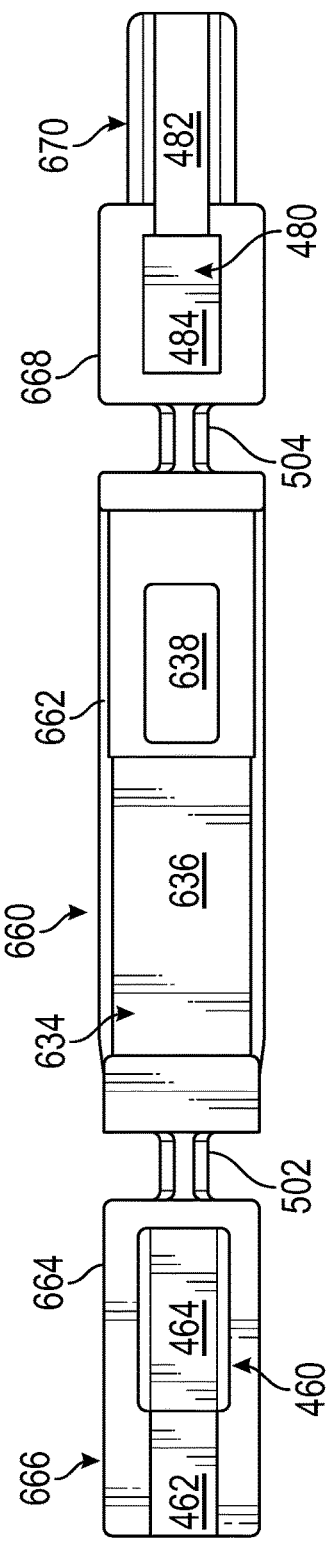
FIG. 21 is a diagrammatic top view of a mounting structure according to another embodiment of the present disclosure.

Referring now to FIG. 21, shown therein is a mounting structure 660 according to another embodiment of the present disclosure. As shown, mounting structure 660 includes a central body 662, a proximal body 664 adjacent a proximal portion 666, and a distal body 668 adjacent a distal portion 670, and various structural features to facilitate interfacing with other components of an intravascular device, such as a guide wire. For example, the central body 662 includes recess 634 and opening 638. The proximal body 664 includes a recess or opening 460 extending from a bottom surface (i.e., opposite of recess 634) that is configured to facilitate coupling of a core to the mounting structure 660. The distal body 668 includes a recess or opening 480 extending from a bottom surface (i.e., opposite of recess 634) that is configured to facilitate coupling of a distal core to the distal body 668. As shown, the proximal body 664 is connected to the central body 662 by a bridge 502, while the distal body 668 is connected to the central body 662 by a bridge 504.

In some implementations for use within a guide wire having an outer diameter of 0.014", the mounting structure 660 has a maximum about 0.125 mm and about 0.400 mm, a maximum width between about 0.28 mm and about 0.50 mm, and a length between about 0.16 mm and about 2.7 mm, with one particular embodiment having a maximum height of about 0.225 mm, a maximum width of about 0.295 mm, and a length of about 1.8 mm. These dimensions can be scaled up or down for larger or smaller diameter guide wires. Further, in the illustrated embodiment, the sides of the mounting structure 660 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 660 will be incorporated.

Referring now to FIG. 22, shown therein is a mounting structure 680 according to another embodiment of the present disclosure. As shown, mounting structure 680 includes a body 682 having a proximal portion 684 and a distal portion 686 with various structural features to facilitate interfacing with other components of an intravascular device, such as a guide wire. For example, the body 682 includes recess 634 and opening 638. The body 682 also includes a recess or opening 560 extending from a bottom surface (i.e., opposite of recess 634) that is configured to facilitate coupling of a core to the mounting structure 680. The distal portion of body 682 is configured to interface with components of the distal tip of the guide wire, such as a distal core, distal coil, and/or other features.

In some implementations for use within a guide wire having an outer diameter of 0.014", the mounting structure 680 has a maximum height between about 0.125 mm and about 0.400 mm, a maximum width between about 0.28 mm and about 0.50 mm, and a length between about 1.5 mm and about 2.2 mm, with some particular embodiments having a maximum height of about 0.2 mm and a maximum width of about 0.295 mm. These dimensions can be scaled up or down for larger or smaller diameter guide wires. Further, in the illustrated embodiment, the sides of the mounting structure 680 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 680 will be incorporated.

Referring now to FIG. 23, shown therein is a mounting structure 690 according to another embodiment of the present disclosure. As shown, mounting structure 690 includes a body 692 having a proximal portion 694 and a distal portion 696 with various structural features to facilitate interfacing with other components of an intravascular device, such as a guide wire. For example, the body 692 includes recess 634 and opening 638. The body 692 also includes a recess or opening 560 extending from a bottom surface (i.e., opposite of recess 634) that is configured to facilitate coupling of a core to the mounting structure 690. The distal portion 696 of body 692 includes a recess or opening 480 extending from a bottom surface (i.e., opposite of recess 634) that is configured to facilitate coupling of a distal core to the body 692.

In some implementations for use within a guide wire having an outer diameter of 0.014", the mounting structure 690 has a maximum height between about 0.125 mm and about 0.400 mm, a maximum width between about 0.28 mm and about 0.50 mm, and a length between about 1.5 mm and about 2.2 mm, with some particular embodiments having a maximum height of about 0.2 mm and a maximum width of about 0.295 mm. These dimensions can be scaled up or down for larger or smaller diameter guide wires. Further, in the illustrated embodiment, the sides of the mounting structure 690 have an overall rounded or arcuate profile (not shown, but see examples with respect to mounting structures 300, 350, and 400 above). In that regard, the radius or rate of curvature of the rounded/arcuate sides is determined based on the desired outer diameter (e.g., 0.014", 0.018", etc.) of the guide wire into which the mounting structure 690 will be incorporated.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A sensing guide wire, comprising:
    a flexible elongate member configured to be positioned within a blood vessel of a patient, the flexible elongate member comprising a proximal portion and a distal portion;
    a mounting structure disposed at the distal portion of the flexible elongate member, the mounting structure comprising a length along a longitudinal axis, wherein the mounting structure comprises a plurality of material layers formed on top of one another, wherein two or more of the plurality of material layers comprise a different width in a direction perpendicular to the longitudinal axis, wherein the different widths of the plurality of material layers together define a size and a shape of an outer profile of the mounting structure; and
    a sensor mounted on the mounting structure,
    wherein the flexible elongate member and the mounting structure each have an outer diameter of between 0.0007" and 0.118".

2. The sensing guide wire of claim 1, wherein the different widths of the plurality of material layers together define a rounded or arcuate shape.

3. The sensing guide wire of claim 1, wherein adjacent material layers comprise the different widths such that the shape is defined in a step-wise manner.

4. The sensing guide wire of claim 1, wherein each of the plurality of material layers comprises an upper surface and a lower surface parallel to the upper surface, and wherein each of the plurality of material layers has a constant thickness along the length.

5. The sensing guide wire of claim 1, wherein each of the plurality of material layers has a same thickness.

6. The sensing guide wire of claim 1, wherein the plurality of material layers comprises at least two layers.

7. The sensing guide wire of claim 1, wherein the plurality of material layers are each formed of a same material.

8. The sensing guide wire of claim 1, wherein at least a subset of the plurality of material layers define a recess sized and shaped to receive the sensor.

9. The sensing guide wire of claim 8, wherein the at least a subset of the plurality of material layers define three wall portions partially surrounding the recess.

10. The sensing guide wire of claim 1, wherein the mounting structure includes a proximal portion, a central portion, and a distal portion;
    wherein the proximal portion of the mounting structure is separated from the central portion of the mounting structure by a proximal bridge comprising a reduced outer profile diameter relative to the proximal and central portions; and
    wherein the central portion of the mounting structure is separated from the distal portion of the mounting structure by a distal bridge comprising a reduced outer profile diameter relative to the central and distal portions.

11. The sensing guide wire of claim 1, wherein the mounting structure includes a first portion and second portion spaced from the first portion by a bridge, wherein the bridge has a reduced outer profile diameter relative to the first and second portions.

12. The sensing guide wire of claim 1, further comprising:
a distal core wire extending within the flexible elongate member and fixedly attached to the mounting structure; and
a proximal core wire fixedly attached to the mounting structure and extending proximally from the mounting structure, wherein the proximal core includes a first section that is fixedly attached to the mounting structure and a second section extending proximally from the first section, wherein the first section is formed of a first material and the second section is formed of a second material.

13. The sensing guide wire claim 12, wherein the second material is different than the first material.

14. The sensing guide wire of claim 12, wherein a distal end of the proximal core wire is positioned within an opening of the mounting structure and fixedly attached to the mounting structure by solder.

15. The sensing guide wire of claim 14, wherein the opening includes a first portion with a first width and a second portion with a second width greater than the first width, wherein the second portion is positioned distal of the first portion.

16. The sensing guide wire of claim 14, wherein the opening includes a first portion and a second portion, the second portion offset with respect to the first portion relative to the longitudinal axis.

17. The sensing guide wire of claim 16, wherein the opening further includes a third portion aligned with the first portion relative to the longitudinal axis, wherein the second portion is positioned between the first and third portions.

18. The sensing guide wire of claim 12, wherein the proximal core wire further includes a third section extending proximally from the second section, wherein the third section is formed of a third material.

19. The sensing guide wire of claim 18, wherein the third material is different than the second material.

20. The sensing guide wire of claim 1, further comprising:
a conductor comprising a proximal section and a distal section, wherein the distal section of the conductor is coupled to the sensor and the proximal section of the conductor is coupled to a connector at the proximal portion of the flexible elongate member.

21. A guide wire, comprising:
a flexible element;
a core member extending within the flexible element;
a mounting structure fixedly secured to the core member, the mounting structure comprising a plurality of material layers formed one on top of another, wherein each of the plurality of material layers comprises a different portion of a shape of the mounting structure and the plurality of material layers together define a recess sized and shaped to receive a pressure sensing component, wherein each of the plurality of material layers comprises an upper surface and a lower surface parallel to the upper surface, wherein each of the plurality of material layers has a constant thickness;
the pressure sensing component mounted to the mounting structure; and
a conductor having a proximal section and a distal section, wherein the distal section of the conductor is coupled to the pressure sensing component and the proximal section of the conductor is coupled to a connector,
wherein the flexible element and the mounting structure each have an outer diameter of between 0.0007" and 0.118".

* * * * *